(12) United States Patent
Miyamura et al.

(10) Patent No.: US 10,914,707 B2
(45) Date of Patent: Feb. 9, 2021

(54) REFERENCE ELECTRODE

(71) Applicant: HORIBA, Ltd., Kyoto (JP)

(72) Inventors: Kazuhiro Miyamura, Kyoto (JP); Yoko Nakai, Kyoto (JP); Yoshihiro Mori, Kyoto (JP); Yoshito Komada, Kyoto (JP); Kimihiko Arimoto, Kyoto (JP); Yuiji Tsujioka, Kyoto (JP); Tomoko Seko, Kyoto (JP); Hiroki Minowa, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 429 days.

(21) Appl. No.: 15/315,180

(22) PCT Filed: Jun. 19, 2015

(86) PCT No.: PCT/JP2015/067737
§ 371 (c)(1),
(2) Date: Nov. 30, 2016

(87) PCT Pub. No.: WO2015/194664
PCT Pub. Date: Dec. 23, 2015

(65) Prior Publication Data
US 2017/0191960 A1    Jul. 6, 2017

(30) Foreign Application Priority Data

Jun. 20, 2014 (JP) ................................ 2014-127753
Dec. 2, 2014 (JP) ................................ 2014-244493

(51) Int. Cl.
*G01N 27/401* (2006.01)
*G01N 27/30* (2006.01)
(Continued)

(52) U.S. Cl.
CPC ....... *G01N 27/4167* (2013.01); *G01N 27/301* (2013.01); *G01N 27/302* (2013.01);
(Continued)

(58) Field of Classification Search
CPC .. G01N 27/301; G01N 27/302; G01N 27/327; G01N 27/36; G01N 27/401;
(Continued)

(56) References Cited

U.S. PATENT DOCUMENTS 3,208,927 A     9/1965  Arthur et al.
3,658,679 A *   4/1972  Stansell ............. G01N 27/4167
                                                  204/403.06
2011/0308947 A1* 12/2011 Wilke .................. G01N 27/403
                                                  204/414

FOREIGN PATENT DOCUMENTS

CN    101196528 A    6/2008
JP    53151985 U     11/1978
(Continued)

OTHER PUBLICATIONS

Google English Machine Translation of Amita et al. (JP61063157U) (provided in Applicant's IDS of Nov. 6, 2019).*
(Continued)

*Primary Examiner* — Maris R Kessel
(74) *Attorney, Agent, or Firm* — Alleman Hall Creasman & Tuttle LLP

(57) ABSTRACT

A reference electrode according to the present invention maintains continuity between an internal solution and measurement sample and measures the electrical potential of the measurement sample even if the measurement sample in a liquid junction of the reference electrode has air bubbles mixed therein. This reference electrode is provided with: a second body provided with a second internal solution chamber in which a second internal solution is housed and a liquid junction portion disposed in the second internal solution chamber such that the second internal solution and measurement sample that is to be measured come into contact; and an internal electrode disposed inside the second internal solution. The liquid junction portion is formed from a
(Continued)

conduction component formed from a porous or fibrous component and an aperture adjacent to the conduction component.

9 Claims, 12 Drawing Sheets

(51) Int. Cl.
G01N 27/416 (2006.01)
G01N 27/327 (2006.01)
G01N 27/36 (2006.01)
G01N 33/487 (2006.01)

(52) U.S. Cl.
CPC ......... *G01N 27/327* (2013.01); *G01N 27/36* (2013.01); *G01N 27/401* (2013.01); *G01N 33/48785* (2013.01)

(58) Field of Classification Search
CPC ......... G01N 27/4167; G01N 33/48785; G01N 27/4166; G01N 27/4117; G01N 27/4035
See application file for complete search history.

(56) References Cited

FOREIGN PATENT DOCUMENTS

| JP | 54008488 U | 1/1979 |
|---|---|---|
| JP | S5547601 U | 3/1980 |
| JP | S5661456 U | 5/1981 |
| JP | 58163867 U | 10/1983 |
| JP | S59183655 U | 12/1984 |
| JP | S603464 U * | 1/1985 |
| JP | S603464 U | 1/1985 |
| JP | 61063157 U | 4/1986 |
| JP | 61161655 U | 10/1986 |
| JP | S62124554 U | 8/1987 |
| JP | 63201562 A | 8/1988 |
| JP | H07306174 A | 11/1995 |
| JP | 10153574 A * | 6/1998 |
| JP | H10153574 A | 6/1998 |
| JP | 2003501656 A | 1/2003 |
| WO | 0075648 A1 | 12/2000 |

OTHER PUBLICATIONS

State Intellectual Property Office of the People's Republic of China, Office Action and Search Report Issued in Application No. 201580028852.4, dated May 17, 2018, 7 pages.

ISA Japan Patent Office, International Search Report Issued in Application No. PCT/JP2015/067737, dated Aug. 25, 2015, WIPO, 4 pages.

Japan Patent Office, Office Action Issued in Application No. 2015234659, dated Aug. 27, 2019, 8 pages.

Japan Patent Office, Office Action Issued in Application No. 2015234659, dated Feb. 4, 2020, 5 pages.

\* cited by examiner

REFERENCE ELECTRODE

TECHNICAL FIELD

The present invention relates to a reference electrode that is used in an electrochemical measurement device such as a pH measurement device.

TECHNICAL BACKGROUND

A measurement electrode and a reference electrode are provided in electrochemical measurement devices that use a glass electrode method beginning with a pH measurement device. Various structures are employed for reference electrodes. For example, in the structure illustrated in Patent document 1, an internal electrode is disposed such that it extends upwards from a bottom end of an internal solution chamber of a reference electrode, and a flow path along which a measurement sample flows horizontally is formed in a space in an upper portion of this internal solution chamber. A partition wall is provided between this flow path and the internal solution chamber. A circular column-shaped liquid junction portion is provided penetrating this partition wall in an up-down direction, and an upper portion of the liquid junction portion is formed as an aperture. Because this aperture is disposed so as to be parallel with the flow of the measurement sample, in a case such as this, if air bubbles are contained in the measurement sample, then the air bubbles flowing along the flow path become caught on the entire aperture and become trapped. If this happens, the air bubbles block conduction between the measurement sample and the internal solution in the liquid junction portion, and the problems arise that it either becomes impossible to measure the potential of the measurement sample, or such measurements become unstable.

Moreover, if a fibrous conduction component such as cloth or the like is provided in the whole liquid junction portion, then air bubbles also become caught and trapped in this cloth. In this case as well, the conduction between the measurement sample and the internal solution in the liquid junction portion is blocked by these air bubbles, and in some cases, the aforementioned problems occur.

DOCUMENTS OF THE PRIOR ART

Patent Documents

Patent Document 1
Japanese Unexamined Utility Model Application Publication No. 59-183655

DISCLOSURE OF THE INVENTION

Problems to be Solved by the Invention

The present invention was therefore conceived in order to solve the above-described problems, and it is a primary object thereof to enable conduction to be maintained between an internal solution and a measurement sample in a liquid junction portion even if air bubbles are mixed in with the measurement sample, and to enable the measurement of the potential of the measurement sample to be performed stably.

Means for Solving the Problem

Namely, a reference electrode according to the present invention includes a body having an internal solution chamber that holds an internal solution, and having a liquid junction portion that is disposed in the internal solution chamber such that the internal solution and a measurement sample that is to be measured are in mutual contact, and an internal electrode that is disposed inside the internal solution chamber, wherein the liquid junction portion is formed by a conduction component that is formed by a porous or fibrous component, and by an aperture that is adjacent to the conduction component.

According to this structure, because the liquid junction portion is formed by a conduction component and by an aperture that is adjacent to this conduction component, when measurement sample flows into the liquid junction portion, it flows easily onto the aperture side which has lower fluid resistance than the conduction component so that, if the measurement sample contains air bubbles, the flow of the measurement sample makes it easy for these air bubbles to become trapped in this aperture rather than in the conduction component.

Accordingly, the conduction component is no longer covered by air bubbles, and because the measurement sample penetrates the porosity or the fibrosity of the conduction component, and is in contact with the internal solution so that the conduction between the measurement sample and the internal solution is maintained, it is possible to measure the potential of the measurement sample in a stable manner.

If the size of the aperture is made larger than the size of the minute holes in the conduction component, then the effects of the present invention can be reliably demonstrated.

Moreover, if air bubbles are contained in the measurement sample, then in order to more reliably ensure that these air bubbles do not become trapped in an end portion of the conduction component that is in contact with the measurement sample, it is preferable for an end portion of the conduction component that is in contact with the measurement sample to be disposed such that this end portion is substantially flush with the aperture, or such that this end portion protrudes onto the measurement sample side beyond the aperture. In particular, if a structure is employed in which the aperture opens onto the flow path traveled by the measurement sample, then if the conduction component protrudes onto the measurement sample side beyond the aperture, then the flow path is made narrower by the end portion of the conduction component and the flow rate of the measurement sample can be speeded up. As a consequence, it becomes even more difficult for air bubbles to becomes trapped at the end portion of the conduction component. At this time, it is desirable for the conduction component to protrude as far as the center of a cross-section of the flow path (i.e., as far as the center of the circle in the case of a flow path having a circular cross-section).

Even if air bubbles do become blocked in the overall liquid junction portion, then in order to make it possible for the internal solution to penetrate the conduction component, it is preferable for the conduction component to be provided such that it extends in the direction of the internal electrode.

Moreover, as a specific example of the placement of the aperture, if the measurement sample flows in one direction through a measurement sample holding portion that holds the measurement sample, then the aperture may be located on a downstream side of the flow of the measurement sample.

As a specific example of the placement of the conduction component in the internal solution chamber, the measurement sample holding portion may be positioned above the internal solution chamber, and above a top end of the internal electrode, and the internal solution chamber may be formed such that a cross-sectional area of the internal solution chamber for a predetermined distance from a top end portion of the internal solution chamber is smaller than a cross-sectional area below the range of this predetermined distance, and the conduction component may be disposed within this predetermined distance from the liquid junction portion.

It is also desirable for there to be further provided a measurement sample holding portion that holds the measurement sample, and a connecting tube that connects together the internal solution chamber and the measurement sample holding portion, and for the connecting tube to be equipped with a base tube portion, a first communicating tube portion that extends upwards from one end of the base tube portion and communicates with the measurement sample holding portion, and a second communicating tube portion that extends upwards from another end of the base tube portion and communicates with the internal solution chamber, or alternatively for the connecting tube to be equipped with a top tube portion, a first communicating tube portion that extends downwards from one end of the top tube portion and communicates with the measurement sample holding portion, and a second communicating tube portion that extends downwards from another end of the top tube portion and communicates with the internal solution chamber.

When the specific gravity of the measurement sample is heavier than that of the internal solution, then if the connecting tube is provided at the lower side in a vertical direction of the measurement sample holding portion, the measurement sample pushes down the internal solution so that this flows into the connecting tube from the measurement sample holding portion. However, because the connecting tube is equipped with the base tube portion, the first communicating tube portion that extends upwards from one end of the base tube portion and communicates with the measurement sample holding portion, and the second communicating tube portion that extends upwards from the other end of the base tube portion and communicates with the internal solution chamber, the inflow of the measurement sample is halted in this base tube portion. Because of this, it is possible to prevent the measurement sample from intruding inside the internal solution chamber, and to prevent the internal electrode housed in the internal solution chamber from being corroded by the measurement sample.

Furthermore, when the specific gravity of the measurement sample is lighter than that of the internal solution, then if the connecting tube is provided at the upper side in the vertical direction of the measurement sample holding portion, the measurement sample pushes up the internal solution so that this flows into the connecting tube from the measurement sample holding portion. However, because the connecting tube is equipped with the top tube portion, the first communicating tube portion that extends downwards from one end of the top tube portion and communicates with the measurement sample holding portion, and the second communicating tube portion that extends downwards from the other end of the top tube portion and communicates with the internal solution chamber, the inflow of the measurement sample is halted in this top tube portion. Because of this, it is possible to prevent the measurement sample from intruding inside the internal solution chamber, and to prevent the internal electrode housed in the internal solution chamber from being corroded by the measurement sample.

Because of this, in the reference electrode of the present invention, it is possible to prevent the internal electrode from being corroded irrespective of the specific gravity of the measurement sample.

It is desirable for the connecting tube to be connected to a lower side in a vertical direction of the measurement sample holding portion.

If this structure is employed, then when calibration is being performed it is possible to prevent the calibration solution which has a lighter specific gravity than the internal solution from flowing into the connecting tube from the measurement sample tube, and any corrosion of the internal electrode that is caused by the calibration solution can be prevented.

It is desirable for there to be further provided a liquid holding component that is provided inside the connecting tube, and for one end of the liquid holding component to be provided in such a way as to be in contact with the conduction component, and for another end of the liquid holding component to be provided in the internal solution chamber.

If this structure is employed, then because the measurement sample or the internal solution soak into the liquid holding component and a state in which these are in mutual contact is maintained, so that the conduction between the measurement sample and the internal solution is maintained, the measurement of the potential of the measurement sample can be performed in a stable manner. As a specific example of this, a hollow fiber that is formed from (for example) a chemically resistant material can be considered.

Effects of the Invention

According to the present invention which is formed in the above-described manner, because a conduction component and an aperture are provided in the liquid junction portion, when measurement sample flows into the liquid junction portion, it flows easily onto the aperture side which has lower fluid resistance than the conduction component so that, if the measurement sample contains air bubbles, the flow of the measurement sample makes it easy for these air bubbles to become trapped in this aperture rather than in the conduction component.

Accordingly, the conduction component is no longer covered by air bubbles, and because the measurement sample penetrates the porosity or the fibrosity of the conduction component, and is in contact with the internal solution so that the conduction between the measurement sample and the internal solution is maintained, it is possible to measure the potential of the measurement sample in a stable manner.

DESCRIPTION OF THE REFERENCE NUMERALS

Figure 1:
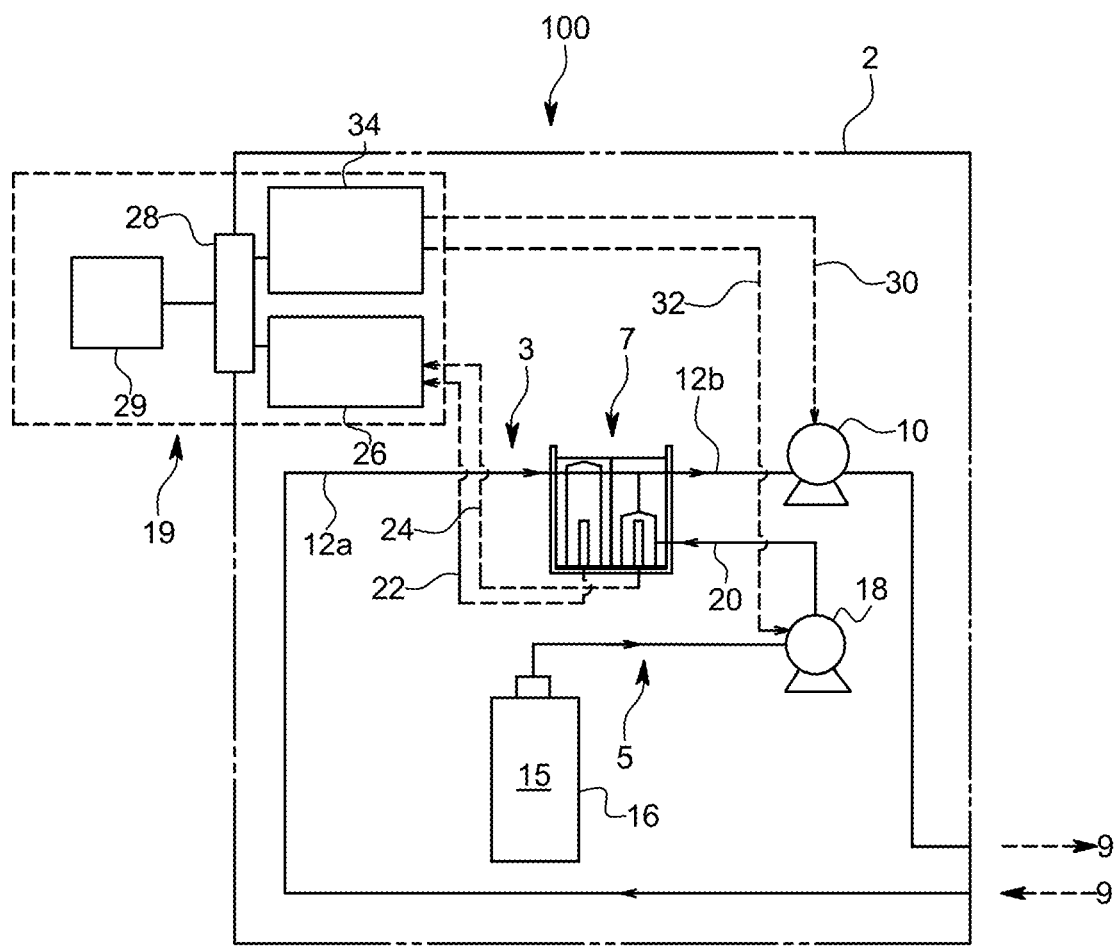
FIG. 1 is an overall typical view of a measurement system according to a first embodiment of the present invention.

100 . . . Measurement system
4, 304, 404, 504 . . . Measurement electrode
6, 306, 406, 506 . . . Reference electrode
7, 307, 407, 507 . . . Electrode apparatus
10 . . . Circulation pump
17 . . . Replenishment aperture
18 . . . Replenishment pump
36 . . . Second internal solution chamber
40 . . . Liquid junction portion
41 . . . Conduction component
42 . . . Second body
45 . . . Aperture
52 . . . First internal solution chamber
54 . . . First body

BEST EMBODIMENTS FOR IMPLEMENTING THE INVENTION

First Embodiment

Hereinafter, a first embodiment of the present invention will be described with reference made to the drawings.

measurement system 100 according to the present embodiment is shown in FIG. 1.

This measurement system 100 is used to continuously monitor a hydrogen ion concentration and the like in a chemical solution (hereinafter, this is also referred to as a 'measurement sample') or the like that is used in a semiconductor manufacturing process, for example, in the cleaning portion of a wiring step, for a Cu plating solution, and for CMP (chemical mechanical polishing) and the like. The measurement system 100 is equipped with an electrode apparatus 7 that measures the pH of a measurement sample 9, a measurement sample circulation mechanism 3 that circulates the measurement sample 9 in the electrode apparatus 7, an internal solution replenishment mechanism 5 that replenishes an internal solution (corresponding to an internal solution of a reference electrode described in Claim 1: referred to below as a 'second internal solution') such as KCl solution or the like in the electrode apparatus 7, and an information processing/control mechanism 19 that is connected to the electrode apparatus 7, the measurement sample circulation mechanism 3, and the internal solution replenishment mechanism 5, and exchanges measurement data and command signals and the like with these. Note that, in addition to hydrogen ions, the measurement system 100 is also able to measure, for example, the ion concentration of sodium, potassium, and the like, and the gas concentration of carbon dioxide, oxygen, and the like ((i.e., $pCO_2$, $pO_2$ and the like).

Figure 2:
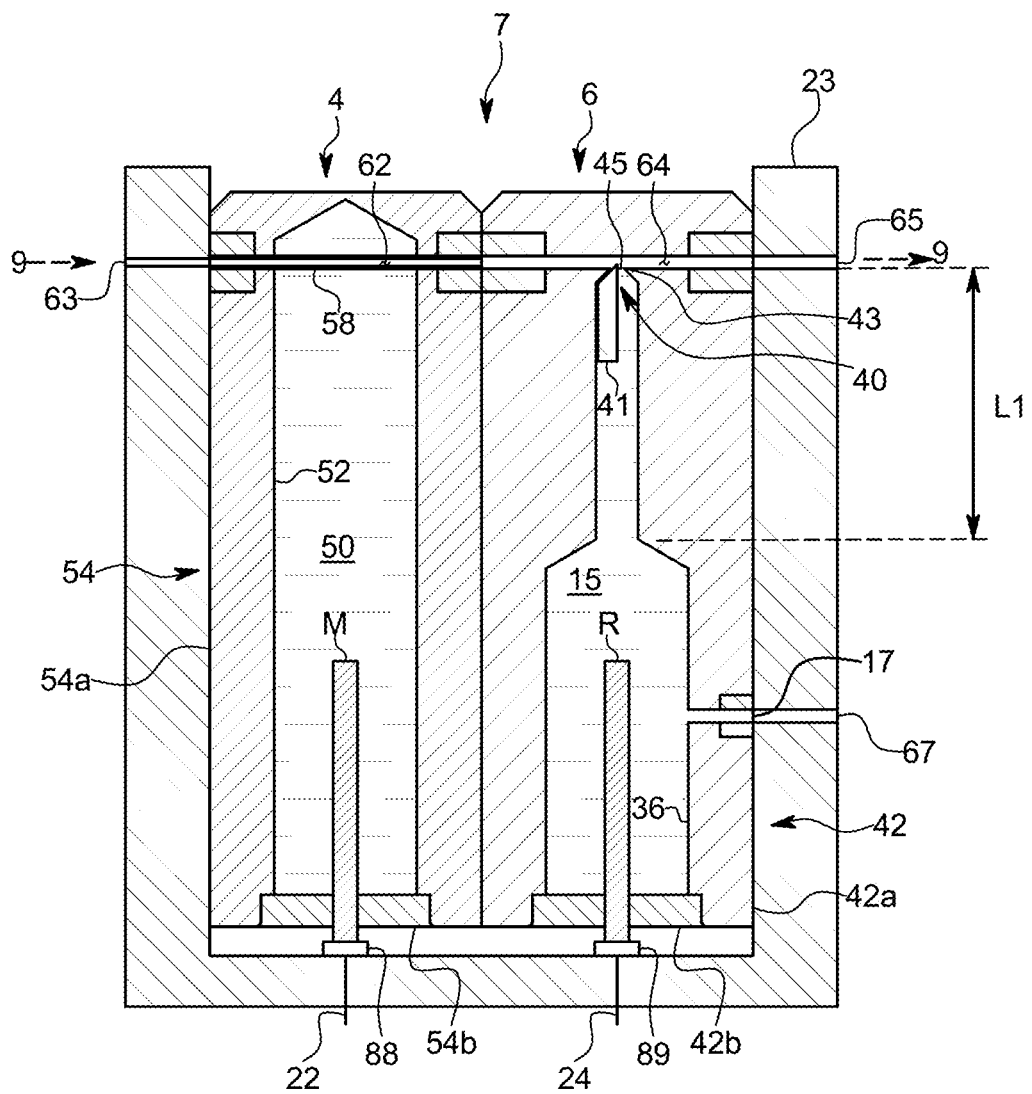
FIG. 2 is a typical view of an electrode apparatus according to the same embodiment.

As is shown in FIG. 2, the electrode apparatus 7 is provided with a measurement electrode 4 and reference electrode 6, and with a frame body 23 that houses these.

The measurement electrode 4 is provided with a first body 54 having a first internal solution chamber 52 in which is contained a predetermined internal solution (hereinafter, referred to as a 'first internal solution') such as a pH buffer solution or the like, and with an internal electrode M that is mounted such that it extends from a lower portion of the first body 54 upwards through the first internal solution chamber 52.

The first body 54 is formed from a material such as PVC (polyvinyl chloride), PP (polypropylene), and PVDF (polyvinylidene & fluoride) and the like, and is formed by a square cylinder-shaped main component 54a that extends in an up/down direction and has a closed top surface and an open bottom surface, and a lid body 54h that closes the bottom surface aperture of the main component. The first internal solution chamber 52 that is formed inside the first body 54 has a uniform cross-sectional configuration (for example, a circular column configuration) from a lower end thereof up to a predetermined height, Only an upper end portion of the first internal solution chamber 52 is formed in a conical configuration whose cross-sectional shape gradually narrows as it moves upwards.

The internal electrode M is formed, for example, by a silver or silver chloride electrode and is mounted such that a lower end portion thereof penetrates the lid body 54b. The internal electrode M stands upright and extends from the lid body 54b upwards through the first internal solution chamber 52. In addition, a contact point is provided on the bottom end of the internal electrode M so that current (voltage) signals can be acquired on the outside via this contact point. Note that the internal electrode M is not limited to a structure in which the bottom end portion of the internal electrode M extends from the lid body 54b, and the internal electrode M may also be formed sloping upwards, or, for example, in an L-shape that extends upwards through the first internal solution chamber 52 from a side surface of the main component 54a.

Furthermore, in this embodiment, the electrode apparatus 7 is also equipped with a tube body 58 along which the measurement sample 9 flows.

The entire tube body 58 is formed from response glass that responds to hydrogen ions, and forms a first flow path 62 along which measurement sample flows. This response glass contains a predetermined quantity of scandium. The tube body 58 is formed in a capillary shape, namely, such that it has a sufficiently long length relative to the internal diameter thereof, and is formed having an extremely narrow shape, for example, having an internal diameter of between approximately 0.1 mm and 2 mm and, more preferably, between approximately 0.5 mm and 1 mm. Moreover, the thickness of the tube body 58 is between approximately 0.1 mm and 1 mm and, more preferably, is approximately 0.2 mm. If the tube body 58 has a thickness such as this, then the response glass has excellent responsiveness. The tube body 58 is also formed having an external diameter of between approximately 0.3 mm and 4 mm and, more preferably, between approximately 1 mm and 2 mm.

This tube body 58 penetrates the top end portion of the first body 54 in a horizontal direction, and is disposed so as to be immersed in a first internal solution 50 inside the first internal solution chamber 52. More specifically, the tube body 58 is disposed above the upper end portion of the internal electrode M and such that it passes through the uniform cross-sectional configuration portion of the first internal solution chamber 52.

Note that it is also possible for response glass to be used for the portion of the tube body 58 that is immersed in the first internal solution 50.

Next, the reference electrode 6 will be described using FIG. 2.

The reference electrode 6 is equipped with a second body 42 (corresponding to a body of a reference electrode described in Claim 1) having an internal solution chamber (corresponding to an internal solution chamber of a reference electrode described in Claim 1: referred to below as a 'second internal solution chamber') in which a second internal solution 15 is contained, an internal electrode R that is mounted such that it extends from a lower portion of the second body 42 upwards through a second internal solution chamber 36, and a replenishment port 17 that is formed in the second body 42 and communicates with the second internal solution chamber 36, and that replenishes the second internal solution 15.

The second body 42 also has a flow path (corresponding to a measurement sample holding portion of a reference electrode described in Claim 5: referred to below as a 'second flow path') along which the measurement sample 9 flows in a horizontal direction above the second body 42, and a liquid junction portion 40 that is disposed in the second internal solution chamber 36 such that the second internal solution 15 and the measurement sample 9 are in mutual contact. This liquid junction portion 40 is formed by a conduction component 41 that is formed by a porous or fibrous component, and an aperture 45 that is adjacent to this conduction component 41.

In the same way as the first body 54 of the measurement electrode 4, the second body 42 is formed from a material such as PVC, and is formed by a square cylinder-shaped main component 42a that extends in an up/down direction and has a closed top surface and an open bottom surface, and a lid body 42b that closes the bottom surface aperture of the main component.

The second internal solution chamber 36 that is formed in the second body 42 has a cylindrical body that is formed so as to extend upwards from a lower portion of the second body 42, and a cross-sectional area of the second internal solution chamber 36 from a top end portion 43 in a downward direction for a predetermined distance L1 while remaining above a top end portion of the internal electrode R is formed smaller than a cross-sectional area below the range of the predetermined distance L1. Furthermore, the volume of the second internal solution chamber 36 from the top end portion 43 of the second internal solution chamber 36 for the predetermined distance L1 is set to less than the quantity of the second internal solution 15 that is replenished via the replenishment aperture 17. The top end portion 43 of this second internal solution chamber 36 is connected to the second flow path 64. Note that, in this embodiment, the top end portion 43 of the second internal solution chamber is formed in a conical shape whose cross-sectional configuration becomes gradually smaller as it moves upwards, however, the present invention is not limited to this and it is also possible to employ a structure in which this cross-sectional configuration remains uniform, and it is sufficient if the measurement sample 9 and the second internal solution 15 are in mutual contact with each other.

Note that the cross-sectional area may be uniform from the top end portion 43 of the second internal solution chamber 36 for the predetermined distance L1, or a structure may be employed in which this cross-sectional area changes, and it is sufficient if this cross-sectional area is formed so as to be smaller than a cross-sectional area of portions below the bottommost position of the predetermined distance L1. In the same way, the cross-sectional area of portions below the bottommost position of the predetermined distance L1 may be uniform, or may change.

A second flow path 64 along which the measurement sample 9 flows is formed above the second body 42. The second flow path 64 is formed extending in a horizontal direction in a top end portion of the second body 42.

The liquid junction portion 40 (described below) is formed such that the measurement sample 9 flowing through the second flow path 64 and the second internal solution 15 are able to be in mutual contact. In this embodiment, a connection hole 49 that is formed in a lower part of an inner side circumferential surface of the second flow path 64, and the top end portion 43 of the second internal solution chamber 36 are connected together. In the present embodiment the connection hole 49 is formed having a substantially circular shape, however, the present invention is not limited to this and it is also possible for the connection hole 49 to have an elliptical configuration or a rectangular configuration.

Note that the second flow path 64 is formed in an upper part of the second body 42, however, the present invention is not limited to this and it is also possible for the second flow path 64 to be formed in a lower part of the second body 42. In this case, the second flow path 64 is connected to a bottom end portion of the second internal solution chamber 36 via the connection hole 49.

Furthermore, in this embodiment, the measurement sample holding portion forms a flow path along which the measurement sample 9 flows, however, the measurement sample holding portion is not limited to this, and may also be formed by a container that holds the measurement sample 9, in which case a structure may be employed in which the second internal solution 15 is able to be in contact with the measurement sample 9 inside this container.

Next, the liquid junction portion 40 will be described using FIG. 3 (a), FIG. 3 (b) and FIG. 4. This liquid junction portion 40 is formed by the conduction component 41 and by the aperture 45 that is adjacent to the conduction component 41. Note that the description of the aperture 45 as being 'adjacent to' the conduction component 41 includes not only cases in which the conduction component 41 and the aperture 45 are placed in contact with each other, but also cases in which, for example, even if a component other than the conduction component 41 is disposed between the conduction component 41 and the aperture 45, then the aperture 45 is still located close enough to the conduction component 41 that air bubbles 47 that have approached the liquid junction portion 40 are able to become trapped in the aperture 45 without covering the conduction component 41. The description of 'close enough' more preferably refers to cases in which the aperture 45 is located a shorter distance to the conduction component 41 than the size of the air bubbles 47 contained in the measurement sample 9.

The conduction component 41 is formed from a porous material having a plurality of minute holes such as, for example, ceramic, polyethylene, a Teflon (registered trademark) membrane or the like, and is disposed such that it is able to be in contact with the measurement sample 9 flowing through the second flow path. The conduction component 41 is a rod-shaped or cord-shaped component that is provided so as to extend in the direction of the internal electrode R, and is disposed above the top end of the internal electrode R so as to extend from the top end portion 43 of the second internal solution chamber 36 for a distance that is within the range of the predetermined distance L1 of the second internal solution chamber 36. Namely, a bottom end portion of the conduction component 41 may be disposed in any location provided that it is between the top end portion 43 and the bottom end of the predetermined distance L1 in the second internal solution chamber 36, and above the top end portion of the internal electrode R.

Note that, if the conduction component 41 is formed in a rod shape, then the bottom end portion thereof may be fixed to an inner circumferential surface of the second internal solution chamber 36 by being adhered thereto by means of an adhesive agent or the like, or, alternatively, the top end portion thereof may be adhered to the top end portion 43 of the second internal solution chamber 36, or, alternatively, an intermediate portion thereof may be adhered to an internal wall surface of the second internal solution chamber 36. If the conduction component 41 is formed in a cord shape, then the top end portion thereof may be fixed to the top end portion 43 of the second internal solution chamber 36 by being adhered thereto by means of an adhesive agent or the like, and, additionally, the intermediate portion thereof may be adhered to the internal wall surface of the second internal solution chamber 36.

Note that if the conduction component 41 is a fibrous component, then it may be formed, for example, from chemical fibers or the like having a plurality of minute holes between the respective fibers.

Moreover, in this embodiment, the conduction component 41 is disposed on the upstream side in the flow direction of the measurement sample 9, however, the present invention is not limited to this, and the conduction component 41 may also be disposed on the downstream side in the flow direction of the measurement sample 9. Alternatively, the conduction component 41 may also be disposed such that the aperture 45 surrounds the periphery of the conduction component 41 in a ring configuration.

Figure 3:
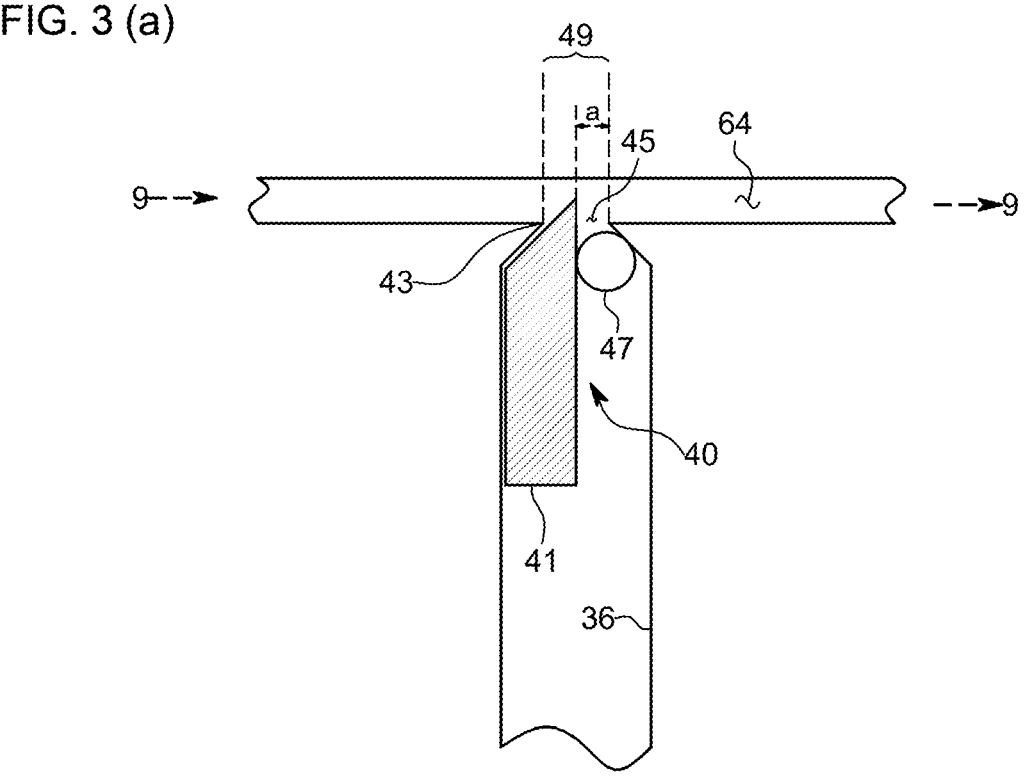
FIGS. 3 (*a*) and 3 (*b*) is a partial enlarged view of a reference electrode according to the same embodiment.
Figure 3:
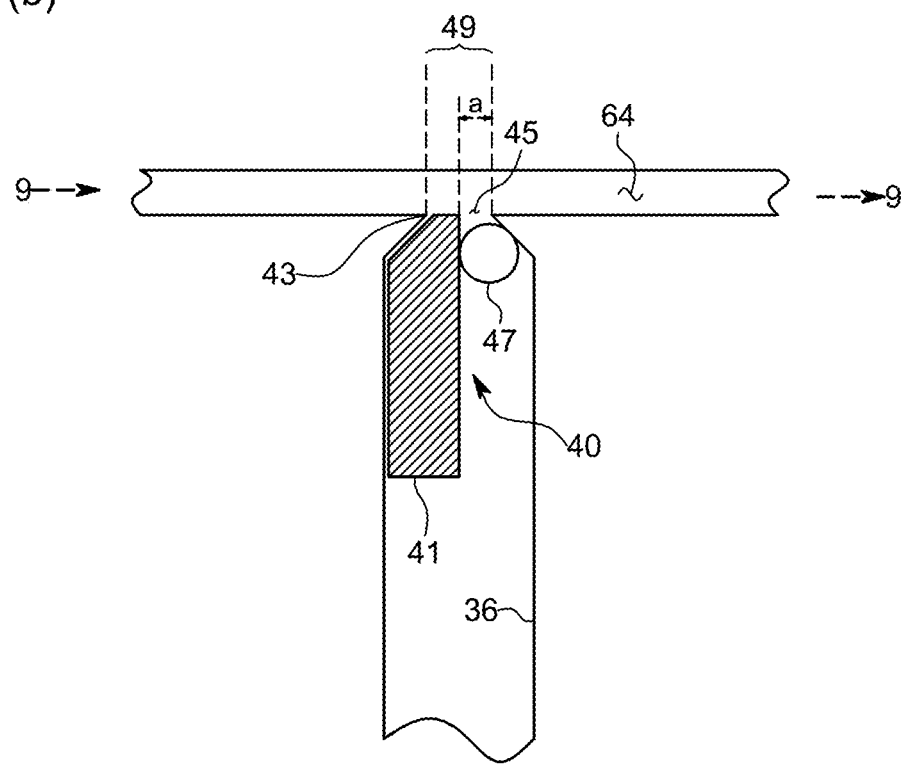
Figure 4:
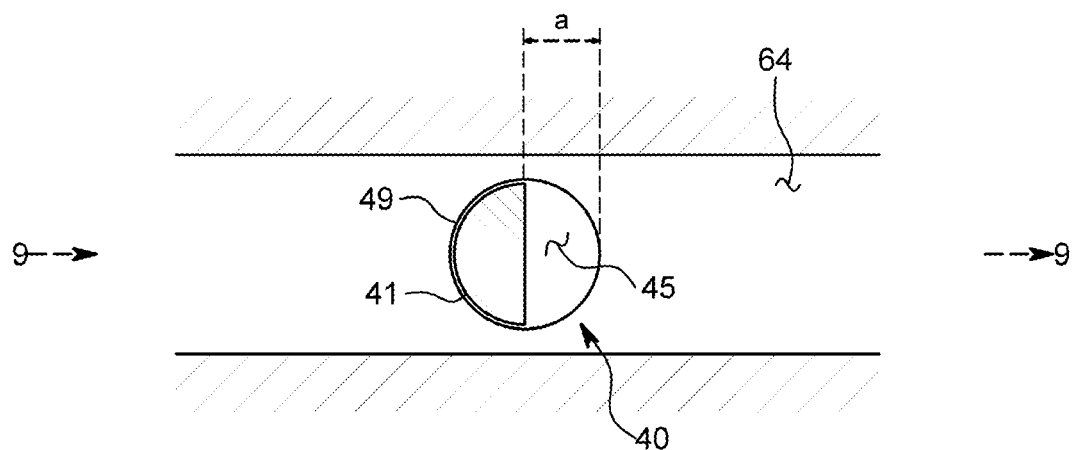
FIG. 4 is a typical plan view of an aperture of the reference electrode according to the same embodiment.

Furthermore, as is shown in FIG. 3 (*a*), the conduction component 41 is also disposed such that the top end portion thereof protrudes beyond the aperture 45 into the second flow path 64. In this embodiment, the top end portion of the conduction component 41 has a shape that becomes narrower as it moves upwards, and protrudes as far as the vicinity of the center in the radial direction of the second flow path 64. Note that the shape of the top end portion is not limited to this, and it is also possible for the top end portion to have a smoothly rounded shape, or a substantially planar shape.

Moreover, as is shown in FIG. 3 (*b*), the conduction component 41 may be disposed such that the top end portion thereof is substantially flush with the aperture 45 and, in this case, the top end portion of the conduction component 41 has a substantially planar shape. Note that the shape of the top end portion of the conduction component 41 is not limited to this and, as is shown in FIG. 3 (*a*), it is also possible for this top end portion to have a narrow tapering shape or, alternatively, a smoothly rounded shape. It is sufficient if the top end portion of the conduction component 41 is positioned substantially flush with the aperture 45.

Moreover, the present invention is not limited to this, and it is sufficient if the top end portion of the conduction component 41 is disposed in a sufficiently lower position than the aperture 45 so that air bubbles do not become trapped in the top end portion.

Note that the structure in which the top end portion of the conduction component 41 protrudes beyond the aperture 45 enables the conduction component 41 to be positioned more easily than when the top end portion is flush with the aperture 45, so that this structure is preferable.

Moreover, the aperture 45 forming the liquid junction portion 40 is connected to the second internal solution chamber 36 and the second flow path 64, and is provided so as to have a width of a dimension a. This dimension a refers to a distance in the aperture 45 from the conduction component 41 to an edge of the aperture 45. If the aperture 45 is formed in a ring shape around the periphery of the conduction component 41, then the dimension a is the size of the width of this ring shape.

This dimension a is set to a larger size than the size of the minute holes in the conduction component 41. A plurality of these minute holes are formed in a variety of shapes such as a substantially circular shape, or a substantially rectangular shape. Generally, because surface tension is acting on the air bubbles so that they are attempting to maintain their spherical shape, a substantially circular shape or a shape close to this, or else an elliptical shape is used for the holes, as such a shape encourages air bubbles to become trapped therein. In addition, if the holes are too small then it becomes difficult for air bubbles to become trapped therein. Therefore, the dimension a is set so as to be larger than the diameter or the major axis of the largest of the minute holes of the conduction component 41 having the above-described shapes. If this type of structure is employed, then the air bubbles 47 easily become trapped in gaps having the dimension a, and it is possible to prevent the air bubbles from covering the conduction component 41.

Note that the dimension a is not limited to being set in this manner, and provided that the shape of the minute holes in the conduction component 41 is a combination of circles and rectangles and the like, then it is sufficient if the dimension a is set so as to be larger than the largest of the diameters of the circular holes, and longer than the longest of the diagonal lines of the rectangular holes. Namely, it is sufficient if the dimension a of the aperture 45 is set so as to be larger than the minute holes in the conduction component 41. If the dimension a is set in this manner, then the air bubbles 47 become trapped in gaps having the dimension a.

The air bubbles 47 contained in the measurement sample 9 are, for example, air bubbles that are generated by pressure variations when the measurement sample 9 is flowing along a flow path, and when a material that tends to generate air bubbles easily such as hydrogen peroxide is contained in the measurement sample 9, then the air bubbles 47 are the bubbles that are generated as a result.

The internal electrode R is formed, for example, by a silver or silver chloride electrode and is mounted such that a bottom end portion thereof penetrates the lid body 42*b*. The internal electrode R stands upright and extends from the lid body 42*b* upwards through the second internal solution chamber 36. In addition, a contact point is provided on the bottom end of the internal electrode R so that current (voltage) signals can be acquired on the outside via this contact point. Note that the internal electrode R is not limited to a structure in which the bottom end portion of the internal electrode R extends from the lid body 42*b*, and the internal electrode R may also be formed sloping upwards, or, for example, in an L-shape that extends upwards through the second internal solution chamber 36 from a side surface of the main component 42*a*.

In the present embodiment, the replenishment port 17 is provided at a position slightly lower than the top end portion of the internal electrode R, however, this can be appropriately modified, and the replenishment port may also be disposed at an even lower position where it is able to replenish the second internal solution 15, for example, from the base portion of the second internal solution chamber 36, or it may be disposed at a position in a central part or in an upper part of the internal electrode R.

Next, the framework body 23 will be described using FIG. 2. The framework body 23 is formed, for example, from resin or metal or the like in a square box shape having an open top side, and the measurement electrode 4 and reference electrode 6 are fitted from above tightly into this framework body.

Contact point portions 88 and 89 with which the respective bottom end portions of the internal electrode M and the internal electrode R are in contact are disposed on a bottom plate of the framework body 23.

An inflow hole 63 that is used to introduce the measurement sample 9 into the tube body 58 which forms part of the first flow path 62 is formed in one side plate of the framework body 23 that is in contact with the measurement electrode 4. Moreover, an outflow hole 65 that enables the measurement sample flowing along the second flow path 64 to be discharged is formed in another side plate of the framework body 23 that is in contact with the reference electrode 6. Furthermore, an inflow hole 67 that introduces the second internal solution 15 into the replenishment port 17 is also formed in the aforementioned other side plate.

As is described above, the electrode apparatus 7 is formed by the measurement electrode 4, the reference electrode 6, and the framework body 23, and the measurement electrode 4 and the reference electrode 6 are housed in the framework body 23 such that the inflow hole 63, the first flow path 62, the second flow path 64, and the outflow hole 65 are in mutual communication, and such that the replenishment port 17 and the inflow hole 67 are in mutual communication. Here, the measurement electrode 4 and the reference electrode 6 are fixed by means of screws or the like (not shown in the drawings) such that they are pressed against each other. As a result of this, the first flow path 62 and the second flow path 64 are connected firmly together, and a structure is created in which the measurement sample 9 is unable to leak from the join between these two flow paths. In order to increase the tightness of the seal between the first flow path 62 and the second flow path 64, it is also possible to provide, for example, an O-ring or the like. Moreover, an adhesive agent or the like is used in the portion where the tube body 58 of the measurement electrode 4 penetrates the first body 54 in order to fix the tube body 58 in this position, and to create a seal that prevents the first internal solution 50 from leaking from the first internal solution chamber 52.

Next, the measurement sample circulation mechanism 3 will be described using FIG. 1 and FIG. 2.

The measurement sample circulation mechanism 3 is provided with an inflow tube 12a that enables the measurement sample 9 to be introduced into the electrode apparatus 7, and an outflow tube 12b through which the measurement sample 9 that passes through the electrode apparatus 7 and is discharged circulates, and with a circulation pump 10 that is disposed at a predetermined location on the inflow tube 12a or the outflow tube 12b, and causes the measurement sample 9 to be introduced and discharged.

The inflow tube 12a is formed such that a distal end portion of the inflow tube 12a is inserted into the inflow hole 63 in the framework body 23, and is connected to the tube body 58 of the measurement electrode 4, and such that the measurement sample 9 is introduced via a base end portion of the inflow tube 12a. The distal end portion of the inflow tube 12a and the tube body 58 of the measurement electrode 4 are connected together and tightly sealed using, for example, an adhesive agent or the like such that the measurement sample 9 can be introduced without leaking into the measurement electrode 4.

The outflow tube 12b is formed such that a base end portion thereof inserted into the outflow hole 65 in the framework body 23, and is connected to the second flow path 64 of the reference electrode 6, and such that the measurement sample 9 is discharged from a distal end portion thereof. The base end portion of the outflow tube 12b and the second flow path 64 of the reference electrode 6 are connected together and tightly sealed using, for example, an adhesive agent or the like such that the measurement sample 9 can be discharged without leaking from the second flow path 64.

Moreover, the circulation pump 10 is disposed in a predetermined location in the inflow tube 12a or the outflow tube 12b, for example, between the base end portion and the distal end portion of the outflow tube 12b. The measurement sample 9 is made to circulate through the inflow tube 12a, the measurement electrode 4, and the reference electrode 6 in that sequence by the operation of the circulation pump 10, and is then made to flow through the outflow tube 12b and is discharged to the outside of the measurement system 100.

Next, the internal solution replenishment mechanism 5 will be described using FIG. 1 and FIG. 2. The internal solution replenishment mechanism 5 is provided with a container 16 that holds the second internal solution 15, a replenishment tube 20 that connects the container 16 to the reference electrode 6 and replenishes the second internal solution 15 in the reference electrode 6, and a replenishment pump 18 that is disposed in a predetermined location on the replenishment tube 20 and causes the second internal solution 15 to circulate. The replenishment tube 20 is formed such that a base end portion thereof is connected to the container 16, and such that a distal end portion thereof is inserted into the inflow hole 67 in the framework body 23 and is connected to the replenishment port 17. The distal end portion of the replenishment tube 20 and the replenishment port 17 of the reference electrode 6 are connected firmly together, for example, by means of an adhesive agent or the like, so that the second internal solution 15 can be introduced into the second internal solution chamber 36 without leaking. Note that, in order to increase the tightness of the seal between the replenishment tube 20 and the replenishment port 17, it is also possible to provide, for example, an O-ring or the like.

The circulation pump 18 is disposed between the base end portion and the distal end portion of the replenishment tube 20. The second internal solution 15 is made to circulate from the container 16 through the replenishment tube 20 by an operation of this replenishment pump 18, and is then used to replenish the reference electrode 6 via the replenishment port 17.

Next, the information processing/control mechanism 19 will be described using FIG. 1 and FIG. 2. The information processing/control mechanism 19 is provided, for example, with a potentiometer 26 that calculates the pH value of the measurement sample 9 that is measured by the electrode apparatus 7, a driver circuit 34 that is provided with circuitry to cause the circulation pump 10 and the replenishment pump 18 to operate, and a control unit 29 that is provided with a computer that processes information obtained from the potentiometer 26 and outputs operation signals and the like to the driver circuit 34, and with a display and the like.

In the present embodiment, a structure is employed in which the control unit 29 is disposed on the outside of a casing 2. Note that the information processing/control mechanism 19 itself may also be disposed on the outside of the casing 2.

The potentiometer 26 is electrically connected by means of internal electrode M wiring 22 and internal electrode R wiring 24 to the internal electrode M of the measurement electrode 4 and the internal electrode R of the reference electrode 6 of the electrode apparatus 7 via the aforementioned contact point portions 88 and 89. As a consequence, based on the respective potentials detected in the internal electrode M and the internal electrode R, the potential difference between the electrodes is measured by the potentiometer 26. The potentiometer 26 is electrically connected to the control unit 29 via an external connection terminal 28. The computer of the control unit 29 calculates the pH value of the measurement sample 9 from output values from the potentiometer 26, and displays these values on the display. The calculated pH values are stored on a storage medium of the computer, and can be displayed whenever this is necessary.

The driver circuit 34 is electrically connected to the circulation pump 10 and the replenishment pump 18 via wiring 30 and 32, and the driver circuit 34 is electrically connected to the control unit 29 via the external connection terminal 28. Based on signals from the computer of the control unit 29, the driver circuit 34 controls the start and stop operations of the circulation pump 10 and the replenishment pump 18, and adjusts the timings at which the measurement sample 9 flows through the electrode apparatus 7, as well as the quantities and the like of these flows. The replenishment quantities of the second internal solution 15, as well as the timings of these replenishments and the like are also controlled such that the measurement system 100 can operate continuously for periods of several months, for example, for between approximately four and eight months.

Figure 5:
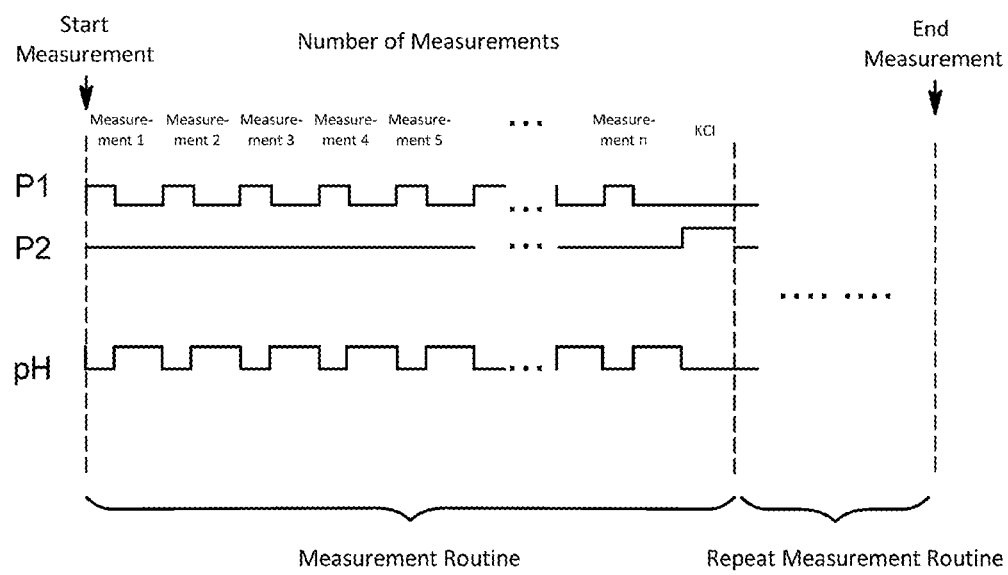
FIG. 5 is a typical view showing a pH measurement sequence according to the same embodiment.

Next, a measurement sequence for measuring the pH of the measurement sample 9 using this measurement system 100 will be described using FIG. 5. A line P1 shows the on and off operation of the circulation pump 10 with peaks showing on times and troughs showing off times. In the same way, P2 shows the on and off operation of the replenishment pump 18. Peak portions of the line pH show when pH measurement is being performed, while trough portions show when pH measurement is not being performed.

Initially, measurement commences after the measurement electrode 4 and the reference electrode 6 have been calibrated (not shown in the drawings). Firstly, a measurement 1 will be described. In this measurement 1, the circulation pump 10 (P1) of the internal solution replenishment mechanism 5 is operated by the information processing/control mechanism 19 for a predetermined time, so that measurement sample 9 is made to flow in the inflow tube 12a and the outflow tube 12b, and this measurement sample 9 flows into the measurement electrode 4 and the reference electrode 6. The quantity of measurement sample 9 that is introduced at this time is, for example, approximately several hundred μL. After the measurement sample 9 has been introduced into the measurement electrode 4 and the reference electrode 6, the circulation pump 10 is temporarily stopped. At this time, the pH measurement is performed.

In this way, the steps of measurement 1 of operating the circulation pump 10, stopping the circulation pump 10, and measuring the pH constitute one measurement, and this measurement is performed n number of times. For example, the pH measurement is performed by repeating this measurement consecutively for approximately 50 to 200 times. After the pH measurement, the circulation pump 10 is stopped by the information processing/control mechanism 19, and the replenishment pump 18 (P2) is operated for a predetermined time so that the second internal solution chamber 36 of the reference electrode 6 is replenished with a predetermined quantity of the second internal solution 15 such as KCl solution or the like from the container 16. The replenishment quantity at this time is a quantity that enables the degree to which the concentration of the second internal solution 15 has become diluted due to the measurement sample 9 flowing into the reference electrode 6 from the liquid junction portion 40 to be restored, and the replenishment quantity of the internal solution is, for example, several tens of μL.

This n number of measurements and replenishment of the second internal solution 15 form one measurement routine, and as a result of this measurement routine being repeated, the replenishment of the second internal solution 15 is performed periodically, and once a predetermined number of measurement routines has ended, the pH measurement is ended.

Because the measurement electrode 4 is formed in the above-described manner, the potential measurement can be performed by causing the measurement sample 9 to flow to the capillary-form tube body 58, so that the quantity of measurement sample 9 that is used for the measurement can be reduced. As a consequence, it is possible to reduce the quantity of chemicals that are discarded after the measurement. In particular, when the circulation pump 10 is stopped so that the circulation of the measurement sample 9 is stopped enabling the potential measurement to be performed, the quantity of chemicals that is used can be reduced even further.

Moreover, even if the temperature of the measurement sample 9 is high, for example, approximately 50°, because the temperature of the measurement sample 9 decreases as it passes through the tube body 58, no convection flow occurs inside the tube body even when the circulation pump 10 is stopped. Because of this, it is possible to prevent irregularities in the measurement of the potential that are caused by a convection flow, and the accuracy of the measurement of the potential can be improved. Moreover, because the circulation pump 10 is stopped, the pH measurement in the measurement electrode 4 and the reference electrode 6 can be performed while the flow of the measurement sample is stopped, so that it is also possible to eliminate any effects on the pH values that are due to the fluidity of the measurement sample.

Moreover, in the present embodiment, because the tube body 58 is disposed above the top end portion of the internal electrode M, and such that it passes through the uniform cross-sectional configuration portion of the first internal solution chamber 52, any air bubbles that are generated in the periphery of the tube body 58 by the pH measurement do not become adhered to the tube body 58, but become trapped in the upper portions of the first internal solution chamber 52. As a consequence, it is possible to prevent any reduction in the measurement accuracy that might be caused by such air bubbles. Note that in the present embodiment, the top end portion of the first internal solution chamber 52 is formed in a conical shape whose cross-sectional configuration becomes smaller as it moves upwards, however, the present invention is not limited to this, and it is also possible for the top surface of the first internal solution chamber 52 to be formed in a planar shape, or in a hemispherical shape, and it is sufficient if a space is formed above the tube body 58 where air bubbles can be trapped.

Moreover, because a predetermined quantity of scandium is contained in the response glass of the tube body 58, it is resistant to hydrofluoric acid, so that even if the chemical being measured is highly acidic and contains hydrofluoric acid, it is still resistant to corrosion and can be used over a prolonged period.

Because the reference electrode 6 has the above-described structure, the air bubbles 47 contained in the measurement sample 9 become trapped in the aperture 45. Accordingly, the conduction component 41 does not become covered by air bubbles and the measurement sample 9 is able to penetrate the porosity or fibrosity of the conduction component 41. Accordingly, because the measurement sample is able to be in contact with the second internal solution 15 so that the conduction between the measurement sample 9 and the second internal solution 15 is maintained, the measurement of the potential of the measurement sample 9 can be performed stably.

A conduction component 41 that is resistant to chemicals is more preferable. If the conduction component 41 is resistant to chemicals, then even if the measurement sample 9 is a highly acidic or a highly alkaline chemical solution, there is no corrosion or the like of the conduction component 41 and it can be used for a prolonged period.

Moreover, because the top end portion of the conduction component 41 is disposed at a lower position than the aperture 45 so as to be substantially flush with the aperture 45, or so as to protrude onto the second flow path 64 side beyond the aperture 45, or such that air bubbles do not become trapped in the top end portion of the conduction component 41, it is possible to avoid a situation in which air bubbles contained in the measurement sample 9 cover the conduction component 41. Accordingly, because the top end portion of the conduction component 41 is able to be in contact with the measurement sample 9, the measurement sample 9 and the second internal solution 15 are in mutual conduction, and measurement of the potential is possible.

Moreover, because the conduction component 41 is provided such that it extends in the direction of the internal electrode R, even if air bubbles become trapped in the entire liquid junction portion 40, the bottom end portion of the conduction component 41 is in contact with the second internal solution 15, and the conduction between the measurement sample 9 and the second internal solution 15 can be maintained.

Moreover, when the bottom end portion of the conduction component 41 is positioned lower than the top end portion of the internal electrode R, during the assembly of the reference electrode 6, when the second internal solution chamber 36 is being filled with the second internal solution 15 from the bottom portion thereof, the second internal solution 15 that has passed over the internal electrode R and arrived at the top end portion thereof, next, reaches the bottom end portion of the conduction component 41. The second internal solution 15 then passes over the conduction component 41 and arrives at the internal wall surface of the second internal solution chamber 36. There is a possibility here that a wall of the second internal solution 15 will be formed between the internal electrode R, the conduction component 41, and this internal wall surface. If this happens, then air builds up on the inner side of this wall, and in some cases the problem arises that these portions cannot be filled with the second internal solution 15.

However, if the conduction component 41 is located above the top end portion of the internal electrode R, and is located within the portion from the top end portion 43 of the second internal solution chamber 36 to the bottom end of the predetermined distance L1, then the aforementioned wall of second internal solution 15 cannot be formed, and the entire second internal solution chamber 36 can be completely filled with the second internal solution 15.

Note that it is also possible for the bottom end portion of the conduction component 41 to be positioned below the top end portion of the internal electrode R, and a structure may also be employed in which the conduction component 41 is shaped so as to follow the internal wall surface of the second internal solution chamber 36, and the conduction component 41 is placed in a position that is separated from the top end portion of the internal electrode R. If this type of structure is employed, the possibility of a wall of the second internal solution 15 being formed between the internal electrode R, the conduction component 41, and the aforementioned internal wall surface is eliminated, and it is possible to reliably fill the second internal solution chamber 36 with the second internal solution 15.

Moreover, because the reference electrode 6 is formed in the manner described above, it is possible to replenish the second internal solution 15 from the replenishment port 17 which is lower than the top end portion of the internal electrode R, and replace the liquid surrounding the internal electrode R with the second internal solution 15. This enables the measurement accuracy to be maintained. In this case, because the measurement sample 9 is introduced from the liquid junction portion 40, and replaces the second internal solution 15 by pushing up the diluted portion of the second internal solution 15, it is sufficient if a quantity of the second internal solution 15 that corresponds to the diluted portion is replenished, so that savings can be made by reducing the replenishment amounts.

The position of the replenishment port 17 can be suitably modified, and it is also possible for the replenishment port 17 to be positioned further down, namely, at the bottom end portion of the second internal solution chamber 36. In this case, even if the specific gravity of the second internal solution 15 is less than that of the measurement sample 9, because the replenishment port 17 is situated at the furthest possible position from the liquid junction portion 40, the replenished second internal solution 15 does not flow out from the liquid junction portion 40, and it is possible to reliably replace the liquid around the internal electrode R with an amount that corresponds to the portion that was diluted by the inflow of the measurement sample 9. As a result, the replenishment quantity of the second internal solution 15 can be economized.

When the specific gravity of the second internal solution 15 is heavier than that of the measurement sample 9, then the replenishment port 17 may be positioned above the top end portion of the internal electrode R. In this case, because the specific gravity of the second internal solution 15 is heavier than that of the measurement sample 9, immediately after the second internal solution 15 has been replenished, there is no outflow of the second internal solution 15 from the liquid junction portion 40 into the measurement sample 9 side, and the weight of the second internal solution 15 causes it to accumulate around the internal electrode R, so that the concentration of the second internal solution 15 around the internal electrode R can be maintained. Furthermore, because the second internal solution 15, which has a heavier specific gravity than the measurement sample 9 is replenished, it is possible to replace the liquid around the internal electrode R with the second internal solution 15 by even more reliably pushing up the portion of the second internal solution 15 that has been diluted by the inflow of the measurement sample 9 from the liquid junction portion 40. Because the replenishment quantity of the second internal solution 15 can be set to a quantity that corresponds to the portion that the second internal solution 15 has become diluted by the inflow of the measurement sample 9, so that the replenishment quantity of the second internal solution 15 can be economized.

Moreover, because the internal electrode R is disposed such that it extends upwards from the bottom end portion of the second internal solution chamber 36, as is the case in the above-described measurement sequence, even if the second internal solution 15 is replenished intermittently by the circulation pump 18 of the internal solution replenishment mechanism 5, because the replacement of the second internal solution 15 is completed before the diluted portion thereof in the upper part of the second internal solution chamber 36 reaches the internal electrode R, the concentration of the second internal solution 15 around the internal electrode R can be maintained. In this way, because the second internal solution 15 can be replenished intermittently, compared with when the replenishment is performed continuously throughout the pH measurement, the quantity of second internal solution 15 that is replenished can be reduced, and the measurement system 100 can be operated continuously for prolonged periods, for example, for between approximately four and eight months without the second internal solution 15 having to be replenished.

Note that it is possible, without completely stopping the replenishment pump 18, to cause it to operate such that the second internal solution 15 flows in minute quantities, and such that quantities of the second internal solution 15 that correspond to the portion that has been diluted by the inflow of the measurement sample 9 are replenished at predetermined intervals, however, as is described above, it is preferable for the replenishment pump 18 to be stopped during pH measurement.

Furthermore, because the cross-sectional area for the predetermined distance L1 from the top end portion 43 of the second internal solution chamber 36 is smaller than the cross-sectional area underneath the bottommost position of the predetermined distance L1, this portion is narrower than the portion where the internal electrode R is located, so that the quantity of the portion of the second internal solution 15 that has been diluted by the inflow of the measurement sample 9 from the liquid junction portion 40 can be reduced even further. Accordingly, the quantity of the portion of the second internal solution 15 that needs to be replaced is reduced, so that the quantity of the second internal solution 15 to be replenished can also be reduced even further.

Moreover, the predetermined distance L1 is readily changed depending on the measurement conditions. For example, after the pH measurement has been performed for a predetermined time, the volume of the portion where the second internal solution 15 has become diluted because of the inflow of measurement sample 9 from the liquid junction portion 40 is taken as V2, and the distance from the top end portion 43 of the second internal solution chamber 36 is taken as L2. If the volume for the predetermined distance L1 in the second internal solution chamber 36 is taken as V1, then a relationship is established for V1 and L1 whereby V2<V1 and L2<L1.

Based on the predetermined distance L1 and on the volume V1 thereof that have been determined in this way, the replenishment quantity of the second internal solution 15 that is to be replenished is determined and, in this case, if the replenishment quantity is taken as V3, and the distance from the top end portion 43 of the second internal solution chamber 36 is taken as L3, then if V3 is set to a quantity whereby a relationship V2<V3<V1 is established, then a further relationship L2<L3<L1 is also established, and the portion that has been diluted by the measurement sample 9 can be replaced with the second internal solution 15.

Furthermore, if the replenishment quantity V3 is set to a quantity whereby a relationship V2<V1<V3 is established, then a further relationship L2<L1<L3 is also established, and the portion that has been diluted by the measurement sample 9 can be adequately replaced with the second internal solution 15. Namely, if the measurement sample 9 has been diffused throughout the area from the top end portion 43 of the second internal solution chamber 36 for the predetermined distance L1 so that the second internal solution 15 has become diluted in this area, then because a quantity of the second internal solution 15 that is greater than this diluted quantity is replenished, this diluted portion can be reliably pushed out from the liquid junction portion 40, and can be replaced with the second internal solution 15.

Note that it is sufficient if the volume V2 of the diluted portion and the volume V3 of the second internal solution 15 are set such that at least a relationship whereby V2<V3 is established.

Next, an electrode apparatus 307 will be described using FIG. 6 as another embodiment of the electrode apparatus 7. Note that symbols in FIG. 6 that are the same as in FIG. 2 indicate structure that is either the same as or corresponds to structure in the previous embodiment.

Figure 6:
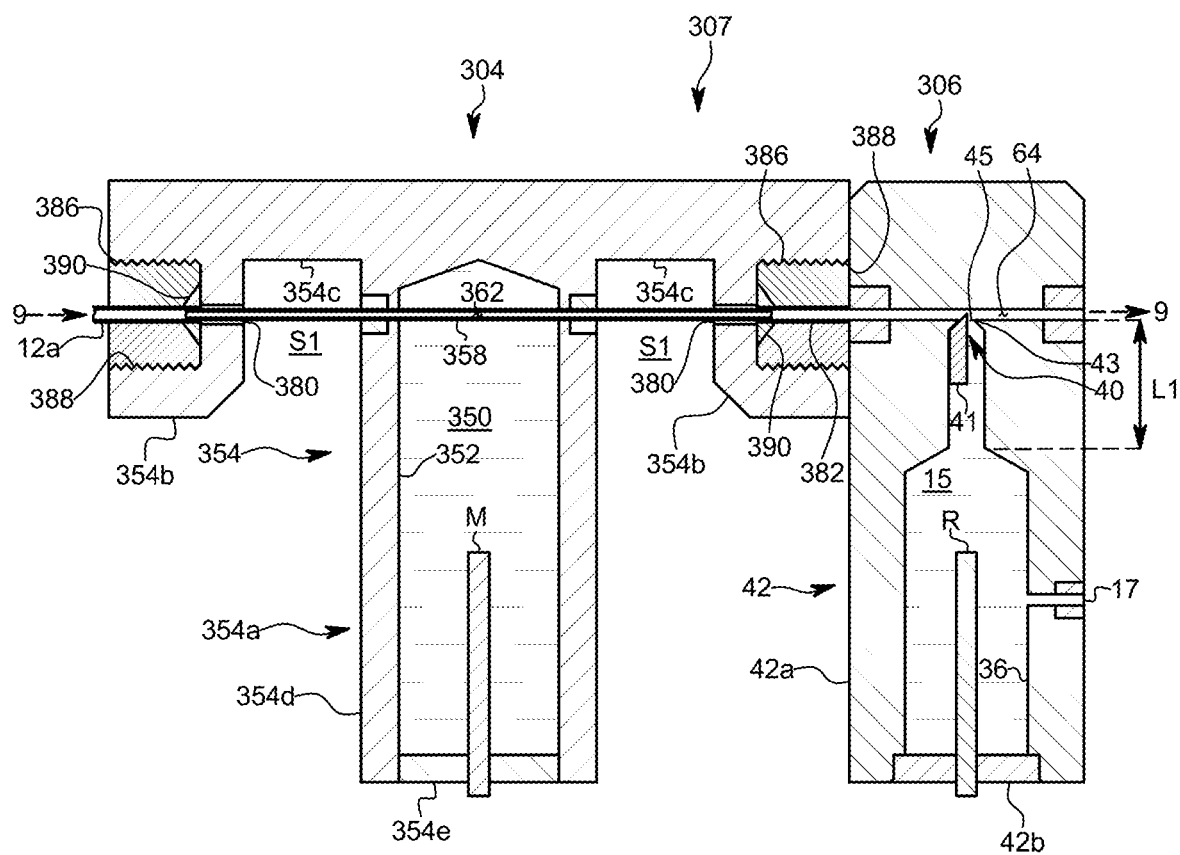
FIG. 6 is a typical view of an electrode apparatus according another embodiment.

As is shown in FIG. 6, the electrode apparatus 307 is provided with a measurement electrode 304 and a reference electrode 306.

The measurement electrode 304 is provided with a first body 354a having a first internal solution chamber 352 that contains a first internal solution 350, sub-bodies 354b that are disposed at a distance from the first body 354a, and linking bodies 354c that link together the first body 354a and the sub-bodies 354b. Furthermore, the measurement electrode 304 is also equipped with an internal electrode M that is mounted such that it extends from a lower portion of the first body 354a upwards through the first internal solution chamber 352. A body 354 of the measurement electrode 304 is formed by the first body 354a, the sub-bodies 354b, and the linking bodies 354c. The material used to manufacture these bodies is the same as the material used to manufacture the first body 54. Moreover, in the same way as the first body 54, the first body 354a is formed by a main component 354d and a lid component 354e, and the first internal solution chamber 352 is formed inside the main component 354d.

The sub-bodies 354b are substantially rectangular block bodies, and a top end portion of one side surface of the first body 354a and a top end portion of one side surface of each sub-body 354b are linked together as a single body by the substantially rectangular box-shaped linking bodies 354c. As a result, the sub-bodies 354b are separated by a predetermined distance from the first body 354a. Spaces S1 having an open lower side are formed between the mutually separated first body 354a and the sub-bodies 354b. In the present embodiment, the sub-bodies 354b are also linked by the linking bodies 354c to another side surface of the first body 354a in the same way, and are disposed at a distance from the first body 354a. Because each of these bodies is formed so as to be linked together in this manner, the measurement electrode 304 has the sub-bodies 354b that are linked together via the linking bodies 354c on both sides of the first body 354a, which is located in the center, so that, when seen in a frontal view, the measurement electrode 304 is formed substantially in a T-shape.

Furthermore, a female threaded hole 388 is formed as a connection port with the reference electrode 306 in each sub-body 354b, and a male threaded component 386, which is an engaging component that engages by being screwed in or out, is disposed in each female threaded hole 388. Furthermore, each female threaded hole 388 and space S1 are in communication with each other via a communication hole 380.

In this embodiment, the measurement electrode 304 is further equipped with a tube body 358 along which the measurement sample 9 flows.

The entire tube body 358 is formed from response glass that responds to hydrogen ions, and forms a first flow path 362 along which measurement sample 9 flows. A downstream side of the first flow path 362 forms an output end side of the tube body 358, while an upstream side of the first flow path 362 forms an input end side of the tube body 358. The material used to form the tube body 358 as well as the shape thereof are the same as for the tube body 58. Moreover, the tube body 358 is disposed in the first body 354a in the same way as the tube body 58 is disposed in the first body 54.

Furthermore, the output end side of the tube body 358 is formed such that it protrudes from the first body 354a, and is inserted into the communication hole 380 in the sub-body 354b. As a consequence, a portion of the tube body 358 is suspended in the space S1 between the first body 354a and the sub-body 354b, and this portion of the tube body 358 is exposed in the space S1.

Moreover, in the present embodiment, the input end side of the tube body 358 also protrudes from the first body 354a, and this input end side is inserted into the communication hole 380 that is formed in the sub-body 354b located at a distance from the aforementioned other side surface of the first body 354a.

Note that it is also possible for response glass to be used for the portion of the tube body 358 that is inserted into the first internal solution 350.

The structure of the reference electrode 306 is the same as that of the reference electrode 6 of the above-described embodiment.

Next, the specific structure of the electrode apparatus 307 will be described. In this electrode apparatus 307, a structure is employed in which the above-described tube body 358 and the second flow path 64 of the reference electrode 306 are connected together by a connecting tube 382, and the measurement sample 9 is supplied from the measurement electrode 304 to the reference electrode 306.

Specifically, another end side of the connecting tube 382 is externally fitted onto the output end side of the tube body 358, and one end side of the connecting tube 382 is connected via a liquid-tight seal to the second flow path 64 by means of an adhesive agent or the like so as to form a flow path for the measurement sample 9. Furthermore, an annular component 390 is provided on the external fitting portion of the connecting tube 382 so as to hold the periphery thereof in position. More specifically, the annular component 390 is an annular component such as a ferrule having a tapered surface, and by screwing the male threaded component 386 into the female threaded hole 388, the male threaded component 386 is abutted against this tapered surface so that the external fitting portion of the connecting tube 382 is pressed by the ferrule, and the connecting tube 382 is fixed to the tube body 358 such that it is unable to separate therefrom.

The distal end portion of the inflow tube 12a is connected to the input end side of the tube body 358, and the measurement sample 9 is introduced into the tube body 358 through the inflow tube 12a. For example, the distal end portion of the inflow tube 12a is externally fitted onto the input end side of the tube body 358 and, in the same way as is described above, a fastening component is provided on this portion so that the inflow tube 12a is fixed to the tube body 358 and is unable to separate therefrom.

The tube body 358 is fixed to the first body 354a by applying an adhesive agent or the like to the portion where the tube body 358 penetrates the first body 354a, and this portion is tightly sealed such that the first internal solution 350 does not leak from the first internal solution chamber 352.

Because the electrode apparatus 307 is formed in the manner described above, even if the first internal solution 350 should leak from the portion where the tube body 358 penetrates the first body 354a as a result of age-related deterioration or the like, because the first internal solution 350 is blocked from being transmitted to the reference electrode 306 in the exposed space area that is provided on the output end side of the tube body 358, it is possible to reliably prevent the first internal solution 350 of the measurement electrode 304 from becoming mixed in the second flow path 64 along which the measurement sample 9 is flowing in the reference electrode 306. The larger this exposed space area, the more reliably the first internal solution 350 can be blocked from being transmitted to the reference electrode 306. Because of this, a longer distance is preferred for the length of the protruding portion.

Moreover, because the measurement electrode 304 is further equipped with the sub-body 354b in addition to the first body 354a, the protruding portion of the tube body 358 can be held by the sub-body 354b.

Furthermore, when the sub-body 354b is linked to the first body 354a by the linking body 354c, then the first body 354a, the sub-body 354b, and the linking body 354c become a single integrated body. Accordingly, the protruding portion of the tube body 358 can be stably held by the sub-body 354b, and it is possible to prevent the tube body 358 from being bent or broken as a result of unanticipated bending force acting on the tube body 358.

Moreover, the distance between the first body 354a and the sub-body 354b is determined by the width of the linking body 354c that links these two together, and this distance can be lengthened by increasing the width of the linking body 354c. As a consequence, the first internal solution 350 can be blocked even more reliably from the reference electrode 306. For example, in cases when a large number of leakages of the first internal solution might be supposed, this type of increased distance is preferable.

Moreover, because the female threaded hole 388 is provided on the side of the sub-body 354b that is in contact with the reference electrode 306 as a connection port with the second flow path 64 of the reference electrode 306, this structure enables the tube body 358 and the connecting tube 382 to be firmly connected together, and enables the measurement sample 9 to be reliably supplied to the second flow path 64.

Moreover, it is also possible to provide a second sub-body and a second linking body on the reference electrode 306, and to enable these to hold the protruding portion of the tube body 358. Specifically, a block-shaped second sub-body is formed via a second linking body on a side surface on the measurement electrode 304 side of the reference electrode 306. By locating the second sub-body at a distance from the second body 42 in this way, the same type of space as that described above is formed. The tube body 358 which is protruding from the first body 354a is held by this second sub-body, and a portion of the tube body 358 is suspended in this space.

If this type of structure is employed, then because the second sub-body is formed via the second linking body on the second body 42 of the reference electrode 306, the tube body 358 can be held without being broken. Moreover, because a structure is employed in which a portion of the tube body 358 is suspended in the space formed by the second body 42 and the second linking body, an exposed space area is provided in the tube body 358 so that the first internal solution 350 can be blocked from being transmitted to the reference electrode 306.

Next, an electrode apparatus 407 will be described using FIG. 7 as yet another embodiment of the electrode apparatus 7.

Figure 7:
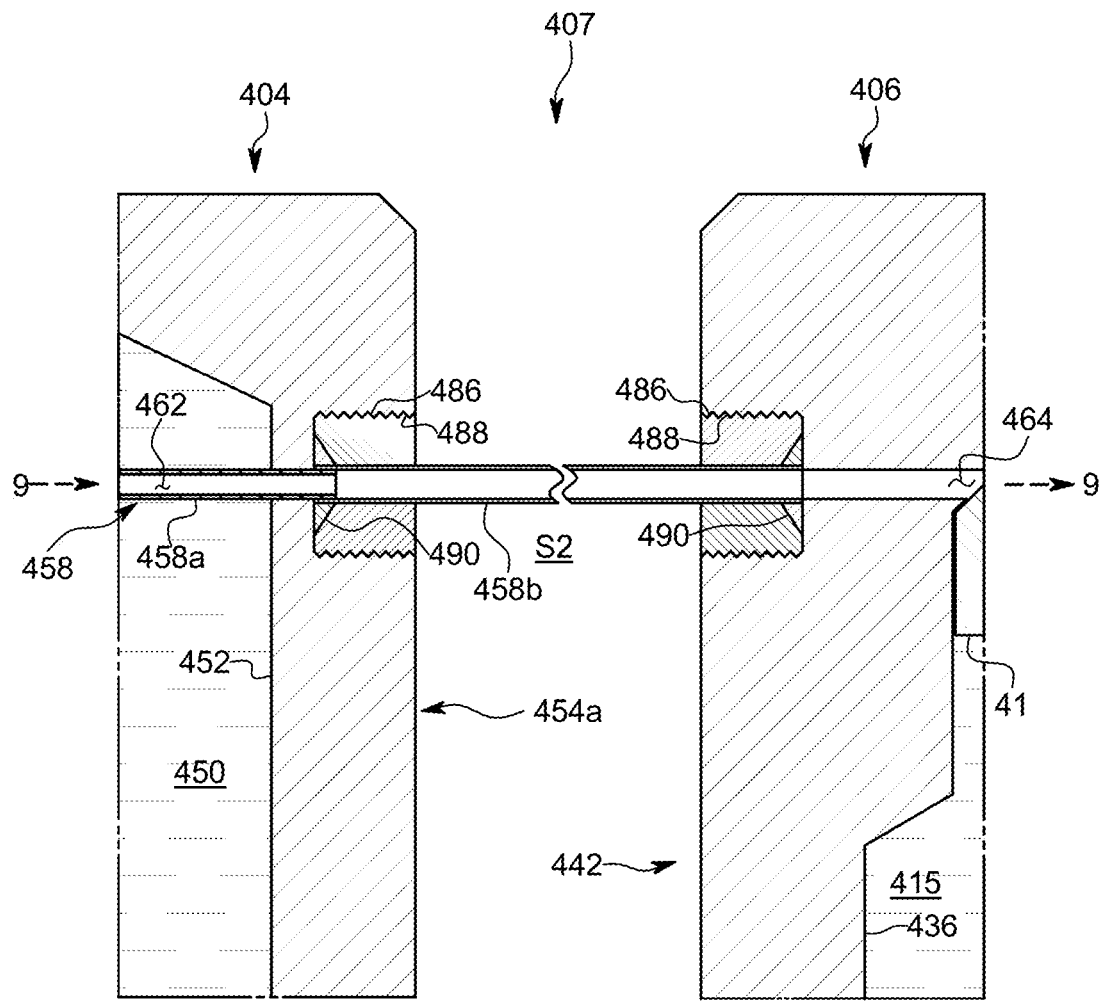
FIG. 7 is a partial enlarged view of an electrode apparatus according to yet another embodiment.

As is shown in FIG. 7, the electrode apparatus 407 is provided with a measurement electrode 404 and a reference electrode 406.

The entire tube body 358 of the above-described electrode apparatus 307 is formed from response glass, however, the tube body 458 of the electrode apparatus 407 is formed by connecting together a plurality of tube body elements, and the tube main elements thereof are a response glass tube 458a that is formed entirely from response glass, and an elastic tube 458b that is made from resin. Namely, a portion of the tube body 458 is formed from response glass. A structure is employed in which an output end side (i.e., one end side of the elastic tube 458b) of this tube body 458 is connected to a second flow path 464 of the reference electrode 406, and the measurement sample 9 is supplied from the measurement electrode 404 to the reference electrode 406. A structure is also employed in which a second internal solution chamber 436 that contains a second internal solution 415 is formed in a second body 442 of the reference electrode 406, and this second internal solution 415 is in contact via a liquid junction portion 440 with the measurement sample 9 that is flowing through the second flow path 464.

Specifically, another end portion of the elastic tube 458b is externally fitted onto one end portion of the response glass tube 458a, and an annular fastening component 490 is provided on the externally fitted portion of the elastic tube 458b that is pressed against the periphery of this externally fitted portion. More specifically, this fastening component 490 is, for example, a conical ferrule having a tapered surface, and a male threaded component 486 is screwed into a female threaded hole 488 that is formed in the first body 454a so as to abut against this tapered surface. As a consequence, the male threaded component 488 is engaged such that it presses against the ferrule, and the externally fitted portion of the elastic tube 458b is also pressed against the ferrule so that this results in the response glass 458a and the elastic tube 458b being connected together.

Because this elastic tube 458b has elasticity, when it is pressed by the ferrule, it becomes tightly adhered to the response glass tube 458a, which is formed from rigid response glass. As a consequence, the connection formed between the response glass 458a and the elastic tube 458b is liquid-tight.

Moreover, the output end side of the tube body 458 (i.e., the one end side of the elastic tube 458b) is also connected in the same way to the second flow path 464 using the fastening component 490 or the like.

A space S2 is formed by separating the measurement electrode 404 from the reference electrode 406, however, because the elastic tube 458b is pliant, when the measurement electrode 404 and the reference electrode 406 are being installed in the measurement system 300, even if the positions of these shift relative to each other, the elastic tube 458b is able to absorb this shift so that assembling the electrode apparatus 407 is made easier.

Because the electrode apparatus 407 is formed in this way, in the same way as the electrode apparatus 307, the first internal solution 450 that is stored in the first internal solution chamber 452 can be prevented from entering the first flow path 462, which is the flow path for the measurement sample 9, and the accuracy of the measurement of the potential can be maintained.

Note that, even if the fastening component 490 is not used, it is still possible, for example, to use an adhesive agent or the like to connect the one end portion of the response glass tube 458a that is protruding from the first body 454a and the other end portion of the elastic tube 458b together with an even greater level of adhesion. Furthermore, the output end side of the tube body 458 may also be tightly connected to the second flow path 464 using an adhesive agent or the like.

Note that, instead of the elastic tube 458b, it is also possible to form the tube body 458 by connecting a rigid, pipe-shaped component to the response glass 458a, and to form the space S2 accordingly.

Furthermore, it is also possible to provide the same type of sub-body and linking body that are used in the measurement electrode 304 in the measurement electrode 404 and the reference electrode 406, and to form the space S2 accordingly so as to hold the tube body 458.

Next, an electrode apparatus 507 will be described using FIG. 8 as yet a further embodiment of the electrode apparatus 7. Note that symbols in FIG. 8 that are the same as in FIG. 6 and FIG. 7 indicate structure that is either the same as or corresponds to structure in the previous embodiments.

Figure 8:
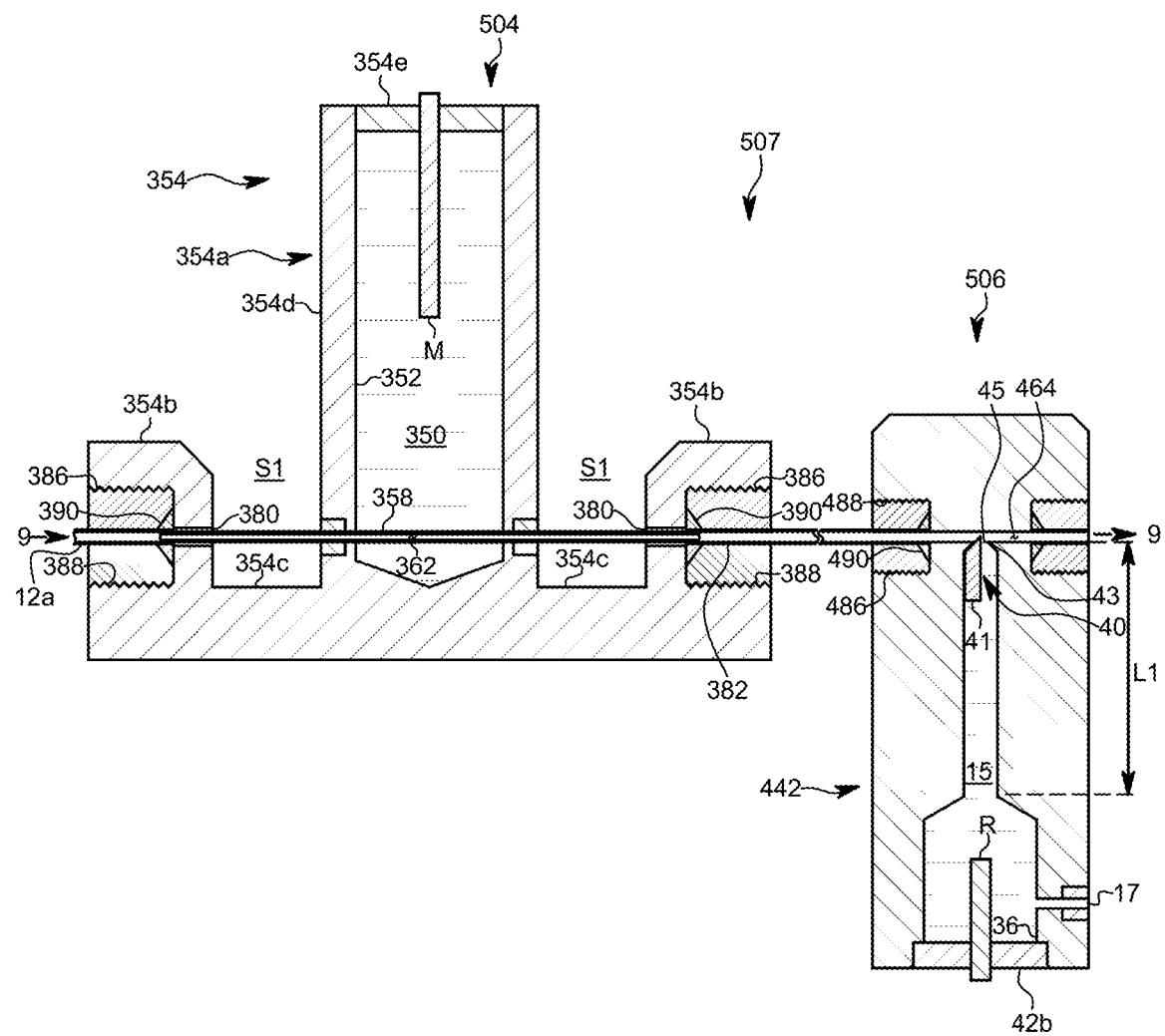
FIG. 8 is a typical view of an electrode apparatus according to yet a further embodiment.

As is shown in FIG. 8, the electrode apparatus 507 is provided with a measurement electrode 504 and a reference electrode 506.

This measurement electrode 504 has the same type of structure as the reference electrode 304, and only differs therefrom in that the measurement electrode 304 is installed after being vertically inverted. Accordingly, a specific description of the structure of the measurement electrode 504 is omitted.

The reference electrode 506 has the same type of structure as the reference electrode 406. Accordingly, a specific description of the structure of the reference electrode 506 is omitted.

Next, the electrode apparatus 507 will be described. In the electrode apparatus 507, the measurement electrode 504 and the reference electrode 506 are disposed at a distance from each other, however, in the same way as in the above-described electrode apparatus 307, a structure is employed in which the tube body 358 and the second flow path 64 of the reference electrode 506 are connected together by the connecting tube 382, and the measurement sample 9 is supplied from the measurement electrode 504 to the reference electrode 506. The structure of the connection between the measurement electrode 504 and the reference electrode 506 in the connecting tube 382 is the same as that used for the measurement electrode 404 and the reference electrode 406, therefore, a specific description thereof will be omitted.

Because the electrode apparatus 507 is constructed in this manner, any air bubbles that are generated by the pH measurement around the tube body 358 that is disposed underneath the first internal solution chamber 532 of the measurement electrode 504 travel towards the upper part of the first internal solution chamber 352 (i.e., towards the lid body 354e). As a consequence, air bubbles do not become attached to the tube body 358 and it is possible to prevent any reduction in the measurement accuracy that is caused by air bubbles.

Second Embodiment

Next, a reference electrode system that incorporates the reference electrode according to the first embodiment will be described, however, different symbols from those used in the first embodiment are employed.

Figure 9:
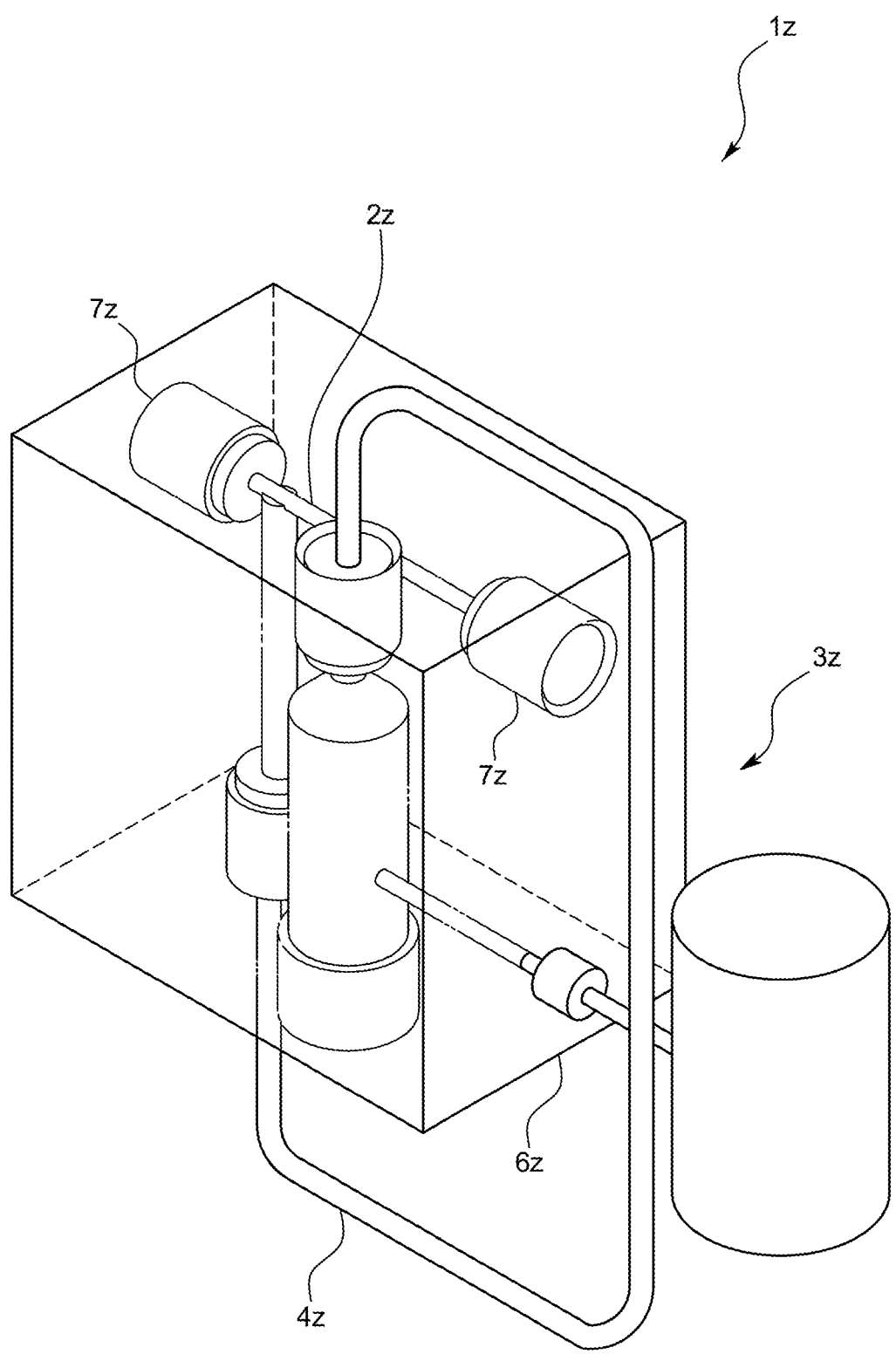
FIG. 9 is a perspective view of a reference electrode according to a second embodiment.
Figure 10:
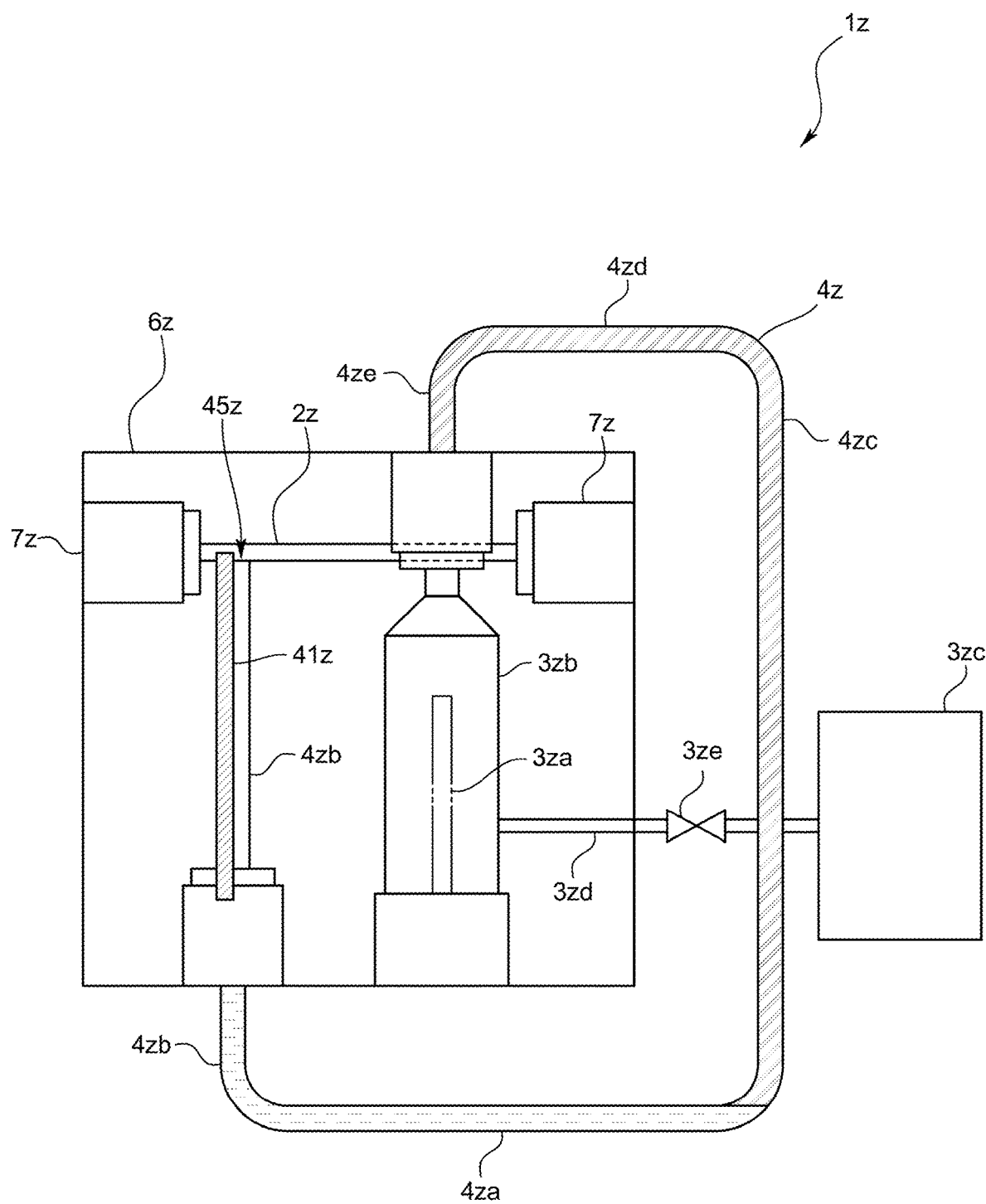
FIG. 10 is a plan view of the reference electrode according to the second embodiment.

As is shown in FIG. 9 and FIG. 10, a reference electrode system 1z according to the second embodiment is equipped with a measurement sample tube 2z which is a measurement sample holding portion along which a measurement sample 9z flows, a reference electrode housing portion 3z that contains an internal solution and is equipped with an internal electrode 3za that is immersed in this internal solution, and a connecting tube 4z that connects the measurement sample 2z to the reference electrode housing portion 3z. Note that in the present embodiment, a portion of each of the measurement sample tube 2z, the reference electrode housing portion 3z, and the connecting tube 4z is housed within a transparent block body 6z.

The measurement sample tube 2z is a flow path along which measurement sample flows, and extends so as to cross horizontally from one side surface to the other side surface of the block body 6z. In the present embodiment, connection fittings 7z that are used to connect to a tank to which the measurement sample is connected, or to a glass electrode or the like are provided on both end portions of the measurement sample tube 2z.

The measurement sample is, for example, a liquid containing a large quantity of solvents such as cleaning solution for semiconductors and the like, and has a specific gravity of approximately 1.19 g/cm³. Note that the measurement sample is not limited to this type, and a variety of measurement samples may be used provided that they are samples for performing electrochemical measurements.

The reference electrode housing portion 3z is equipped with a substantially cylinder-shaped holding vessel (internal solution chamber) 3zb, the internal electrode 3za that is made, for example, from AgCl or the like and is disposed so as to stand upright inside the holding vessel 3zb, internal solution that is held in the holding vessel 3zb and in which the internal electrode 3za is immersed, a tank 3zc that holds the internal solution, a supply tube 3zd that links together the holding vessel 3zb and the tank 3zc and supplies internal solution to the holding vessel 3zb, and a valve 3ze that opens and closes the supply tube 3zd. This holding vessel 3zd is disposed such that it penetrates from a top surface of the block body 3z to a bottom surface thereof.

The internal solution is, for example, a 3.3 mol KCl solution or the like, and has a specific gravity of 1.17 g/cm³ which is less than the specific gravity of the measurement sample. Note that the above-described electrode 3za and the internal solution are not limited to those described above, and may be appropriately altered to suit samples for performing electrochemical measurements.

As is shown in FIG. 10, the connecting tube 4z connects the measurement sample tube 2z to the reference electrode housing portion 3z and, in the present embodiment, is equipped with a base tube portion 4za, a top tube portion 4zd, a first communicating tube portion 4zb that extends upwards from one end of the base tube portion 4za and communicates with the measurement sample tube 2z, a second communicating tube portion 4zc that extends upwards from another end of the base tube portion 4za and communicates with the top tube portion 4zd (i.e., that extends downwards from one end of the top tube portion 4zd, and communicates with the base tube portion 4za), and a third communicating tube 4ze that extends downwards from another end of the top tube portion 4zd and communicates with the holding vessel (i.e., the internal solution chamber) 3zb.

The base tube portion 4za, a portion of the first communicating tube portion 4zb, the second communicating tube portion 4zc, the top tube portion 4zd, and the third communicating tube 4ze are disposed on the exterior side of the block body 6z, and are formed by tubes. Note that a remaining portion of the first communicating tube portion 4zb is housed inside the block body 6z.

The other portion of the first communicating tube portion 4zb (namely, an upper side portion of the first communicating tube portion 4zb) is connected to the measurement sample tube 2z, and the connection portion between these forms a structural liquid junction portion 45z. Moreover, in the same way as in the first embodiment, a conduction component 41z is provided in an upper-side portion of the first communicating tube portion 4zb.

An operation of the reference electrode system 1z that is formed in the manner described above will now be described.

Firstly, when the valve 3ze provided in the reference electrode housing portion 3z is opened and internal solution is supplied to the holding vessel 3zb, the interior of the holding vessel 3zb is filled with the supplied internal solution which then travels through the connecting tube 4z and arrives at the connection portion between the measurement sample tube 2z and the connecting tube 4z. Next, the valve 3ze is closed and the supplying of the internal solution is stopped. This step is called a measurement commencement step.

Measurement sample is then allowed to flow to the measurement sample tube 2z. When the specific gravity of this measurement sample is heavier than that of the internal solution, the measurement sample flows in from the structural liquid junction portion 45z, pushes down the internal solution, and flows out from the measurement sample tube 2z into the first communicating tube portion 4zb and the base tube portion 4za, however, because the two ends of the base tube portion 4za communicate with the upwardly-extending first communicating tube portion 4zb and the second communicating tube portion 4zc, the outflow is stopped at the base tube portion 4za. A liquid junction portion is essentially created in this outflow stop position where the measurement sample and the internal solution are in mutual contact. As a result of this liquid junction portion being generated, the internal electrode 3za is electrically connected to the measurement sample, and manifests the functions of a reference electrode. This step is called a measurement step.

Next, the reference electrode system 1z is calibrated.

When the inflow of measurement sample has been stopped, the valve 3ze is opened and internal solution is allowed to flow from the holding vessel (i.e., the internal solution chamber) 3zb to the measurement sample tube 2z via the connecting tube 4z so that the remaining measurement sample is pushed out to the connecting tube 4z and the measurement sample tube 2z. This step is called a calibration preparation step. In this calibration preparation step, any measurement sample remaining in the connecting tube 4z can be removed, and any deterioration in the measurement accuracy can be prevented.

When a predetermined time has elapsed, the valve 3ze is closed. While the supply of internal solution is stopped, calibration solution is allowed to flow into the measurement sample tube 2z. This step is called a calibration step. At this time, because the connecting tube 4z is connected to a lower side in a vertical direction of the measurement sample tube 2z, the calibration solution which has a lighter specific gravity than the internal solution is unable to flow into the connecting tube 4z, and the internal electrode 3xa can be prevented from being corroded by the calibration solution.

Lastly, after the inflow of calibration solution has been stopped, the valve 3ze is opened and the internal solution is allowed to flow in. The sequence then returns to the measurement commencement step. In the above-described operating sequence, the valve 3ze is in an open state in the measurement commencement step and the calibration preparation step.

According to the reference electrode system 1z of the second embodiment which is formed in the manner described above, the following effects are obtained.

When the specific gravity of the measurement sample is heavier than that of the internal solution, the measurement sample pushes down the internal solution so that this flows into the connecting tube 4z that is connected to the lower side in the vertical direction of the measurement tube 2z. However, because the connecting tube 4z is equipped with the base tube portion 4za, and the first communicating tube portion 4zb and second communicating tube portion 4zc that extend upwards from both ends of the base tube portion 4za, the inflow of the measurement sample is halted in this base tube portion 4za. Because of this, it is possible to prevent the measurement sample from intruding inside the holding vessel (i.e., the internal solution chamber) 3zb, and to prevent the internal electrode 3za housed in the holding vessel (i.e., the internal solution chamber) 3zb from being corroded by the measurement sample.

In order to prevent the measurement sample from intruding inside the holding vessel (i.e., the internal solution chamber) 3zb, continuously feeding in internal solution so as to prevent the intrusion of the measurement sample by using the pressure of the internal solution might be considered, however, because the connecting tube 4z is formed in the manner described above, even if the internal solution is not continuously supplied, it is still possible to prevent the measurement sample from intruding into the holding vessel 3zb. As a consequence of this, because it is possible to operate the valve 3ze intermittently and reduce the quantity of internal solution that is used, the size of the tank holding the internal solution can be reduced, and the number of time the internal solution is supplied to the tank can also be reduced so that the burden on a user can be alleviated. In addition, because the quantity of internal solution that is used is reduced, costs can also be kept in check.

Furthermore, because the reference electrode system 1z is formed by the block body 6z and some tubes, compared with when the entire structure is provided inside the block body 6z, the structure can be made simpler and manufacturing costs can also be kept low. Moreover, compared with when the entire structure is provided inside the block body 6z, the size of the block body 6z can be reduced so that the measurement sample tube, the reference electrode housing portion, the connecting tubes and the like can also be reduced in size, and measurements can be made in spite of the fact that the quantities of measurement sample and internal solution that are used are reduced.

Third Embodiment

Next, a third embodiment of the present invention will be described, however, portions that are the same as in the second embodiment are given the same descriptive symbols and a description thereof is omitted.

Figure 11:
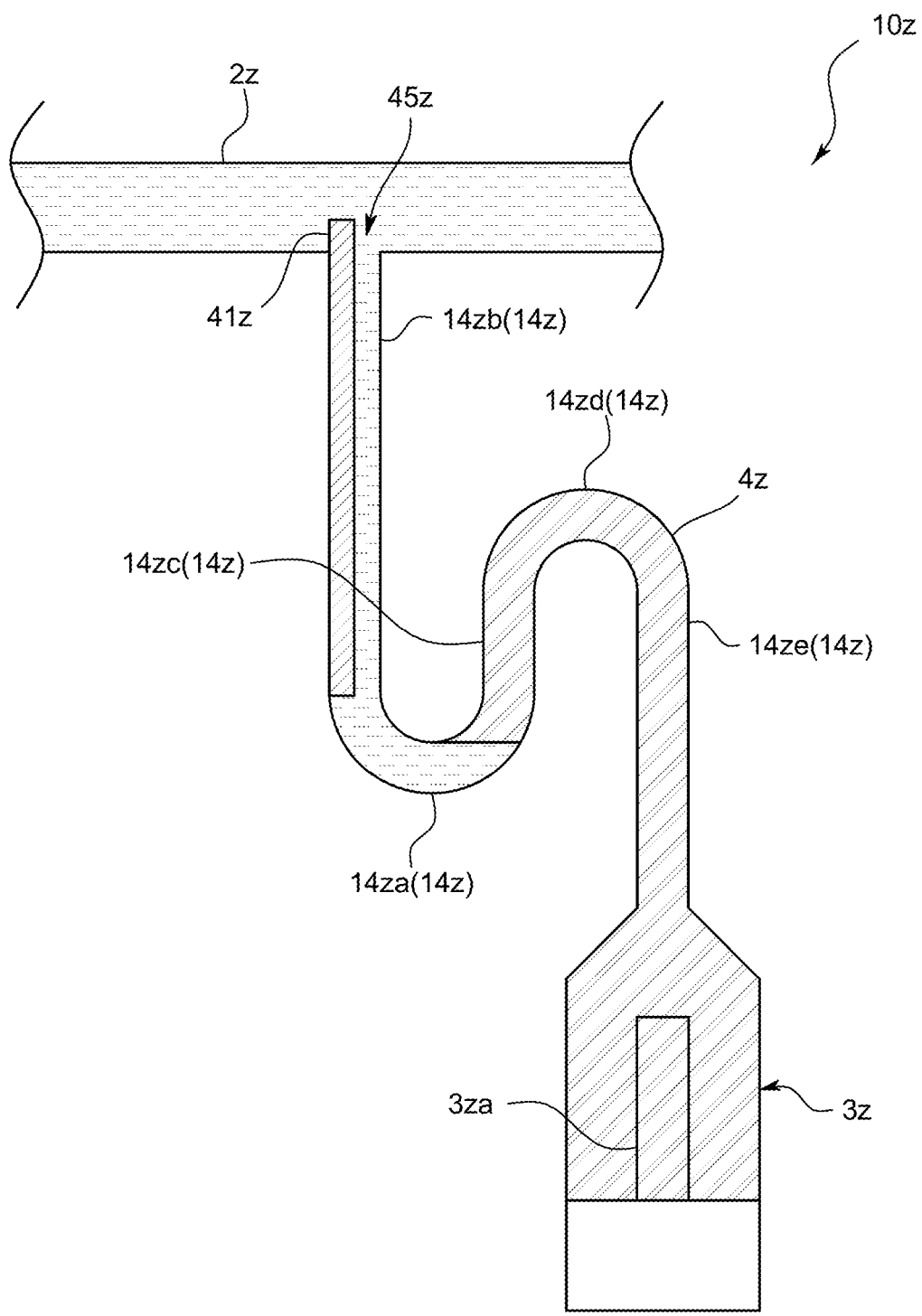
FIG. 11 is a schematic view of a reference electrode according to a third embodiment.

As is shown in FIG. 11, in a reference electrode system 10z of the third embodiment, the structure of the connecting tube 14z differs from that of the first embodiment. The connecting tube 14z of the third embodiment is equipped with a base tube portion 14za, a top tube portion 14zd, a first communicating tube portion 14zb that extends upwards from one end of the base tube portion 14za and communicates with the measurement sample tube 2z, a second communicating tube portion 14zc that extends upwards from another end of the base tube portion 14za and communicates with the top tube portion 14zd (i.e., that extends downward from one end of the top tube portion 14zd, and communicates with the base tube portion 14za), and a third communicating tube portion 14ze that extends downwards from another end of the top tube portion 14zd and communicates with the holding vessel (i.e., the internal solution chamber) 3zb.

The base tube portion 14za, the first communicating tube portion 14zb, and the second communicating tube portion 14zc together are formed substantially in a U-shape that protrudes in a downward direction, while the top tube portion 14zd, the second communicating tube portion 14zc, and the third communicating tube portion 14ze together are formed substantially in a U-shape that protrudes in an upward direction. The base tube portion 14za, the first communicating tube portion 14zb, the second communicating tube portion 14zc, the top tube portion 14zd, and the third communicating tube 14ze are all formed by tubes.

A connection portion between an upper-side portion of the first communicating tube portion 14zb and the measurement sample tube 2z forms the structural liquid junction portion 45z. Moreover, in the same way as in the first embodiment, the conduction component 41z is provided in an upper-side portion of the first communicating tube portion 14zb.

When the specific gravity of the internal solution is lighter than that of the measurement sample, the measurement sample flows in from the structural liquid junction portion 45z, pushes down the internal solution, and flows into the connecting tube 4z that is connected to the lower side in the vertical direction of the measurement sample tube 2z. However, because the first communicating tube portion 14zb and the second communicating tube portion 14zc that communicate respectively with the two ends of the base tube portion 14za both extend upwards, the intrusion of the measurement sample is stopped at the base tube portion 14za. A liquid junction portion is essentially formed in this position where the measurement sample and the internal solution are in mutual contact.

In the reference electrode system 10z of the third embodiment that is provided in this way as well, because the reference electrode system 10z is equipped with the base tube portion 14za and the first communicating tube portion 14zb and second communicating tube portion 14zc that extend upwards from both ends of the base tube portion 14za, the inflow of the measurement sample is halted in this base tube portion 14za. Because of this, it is possible to prevent the measurement sample from intruding inside the holding vessel (i.e., the internal solution chamber) 3zb, and to prevent the internal electrode housed in the holding vessel (i.e., the internal solution chamber) 3zb from being corroded by the measurement sample.

Fourth Embodiment

Next, a fourth embodiment of the present invention will be described, however, portions that are the same as in the first embodiment and second embodiment are given the same descriptive symbols and a description thereof is omitted.

Figure 12:
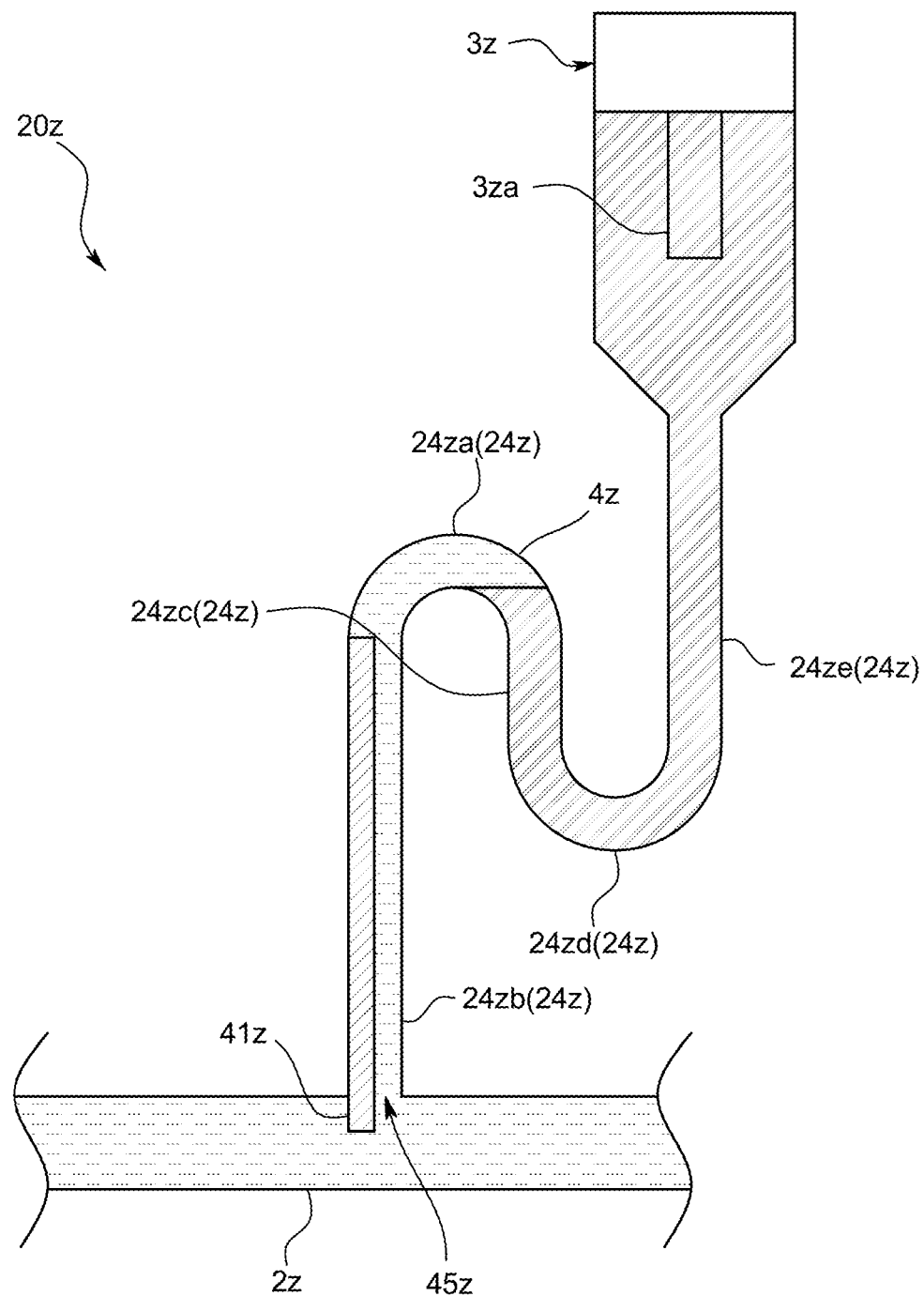
FIG. 12 is a schematic view of a reference electrode according to a fourth embodiment.

As is shown in FIG. 12, in a reference electrode system 20z of the fourth embodiment, the structure of a connecting tube 24z and a connecting portion between the connecting tube 24z and the measurement sample tube 2z differ from those of the second embodiment and the third embodiment.

Namely, the connecting tube 24z is equipped with a top tube portion 24za, a base tube portion 24zd, a first communicating tube portion 24zb that extends downwards from one end of the top tube portion 24za and communicates with the measurement sample tube 2z, a second communicating tube portion 24zc that extends downwards from another end of the top tube portion 24za and communicates with the base tube portion 24zd (i.e., that extends upwards from one end of the base tube portion 24zd, and communicates with the top tube portion 24za), and a third communicating tube portion 24ze that extends upwards from another end of the base tube portion 24zd and communicates with the holding vessel (i.e., the internal solution chamber) 3zb.

The top tube portion 24za, the first communicating tube portion 24zb, and the second communicating tube portion 24zc together are formed substantially in a U-shape that protrudes in an upward direction, while the base tube portion 24zd, the second communicating tube portion 24zc, and the third communicating tube portion 24ze together are formed substantially in a U-shape that protrudes in a downward direction.

This connecting tube 24z is connected to the upper side in the vertical direction of the measurement sample tube 2z.

A connection portion between a lower-side portion of the first communicating tube portion 24zb and the measurement sample tube 2z forms the structural liquid junction portion 45z. Moreover, in the same way as in the first embodiment, the conduction component 41z is provided in a lower-side portion of the first communicating tube portion 24zb.

When the specific gravity of the internal solution is heavier than that of the measurement sample, the measurement sample flows in from the structural liquid junction portion 45z, pushes up the internal solution, and flows into the connecting tube 4z that is connected to the upper side in the vertical direction of the measurement sample tube 2z. However, because the first communicating tube portion 24zb and the second communicating tube portion 24zc that communicate respectively with the two ends of the top tube portion 24za both extend downwards, the inflow of the measurement sample is stopped at the top tube portion 24za. A liquid junction portion is essentially formed in this position where the measurement sample and the internal solution are in mutual contact.

In the reference electrode system 20z of the fourth embodiment that is provided in this way as well, because the reference electrode system 20z is equipped with the top tube portion 24za and the first communicating tube portion 24zb and second communicating tube portion 24zc that extend downwards from both ends of the top tube portion 24za, the inflow of the measurement sample is halted in this top tube portion 24za. Because of this, it is possible to prevent the measurement sample from intruding inside the holding vessel (i.e., the internal solution chamber) 3zb, and to prevent the internal electrode 3za housed in the holding vessel (i.e., the internal solution chamber) 3zb from being corroded by the measurement sample.

Furthermore, when the connecting tube 4z is provided on the upper side in the vertical direction of the measurement sample tube 2z, then when calibration is performed, the calibration solution which has a lighter specific gravity than the internal solution flows from the measurement sample tube 2z into the connecting tube 4z, however, because the inflow of this calibration solution is stopped by the above-described structure in the top tube portion 24za, the calibration solution can be prevented from corroding the internal electrode 3za.

Note that the present invention is not limited to the above-described first through fourth embodiments.

Figure 13:
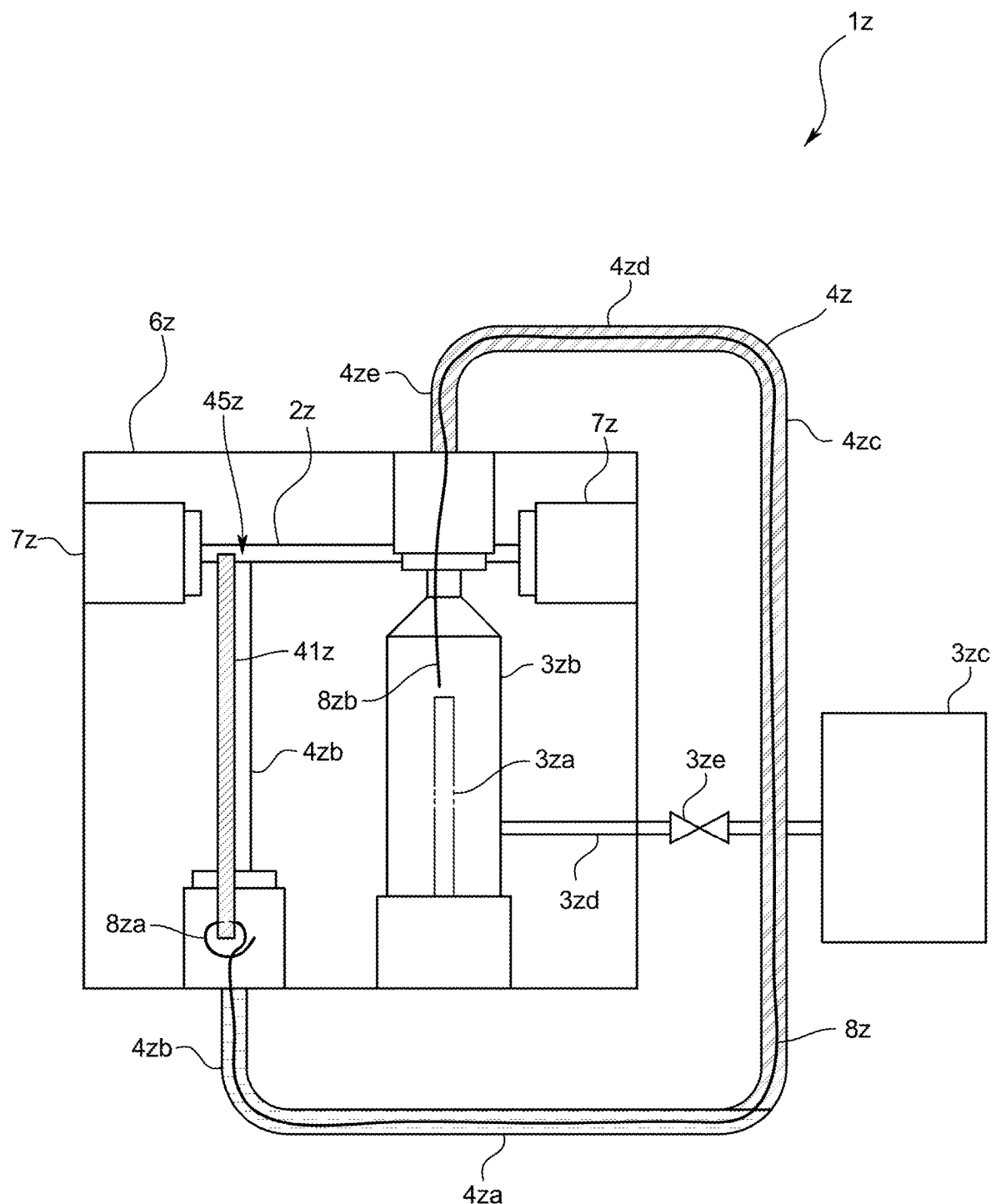
FIG. 13 is a schematic view of a reference electrode according to a fifth embodiment.

For example, in the above-described second through fourth embodiments, it is also possible to provide a liquid holding component 8z inside the connecting tube 4z. Specifically, as is shown in FIG. 13, the liquid holding component 8z is provided such that one end 8za thereof is in contact with the conduction component 41z, and such that another end 8zb thereof is provided inside the internal solution chamber 3zb. A structure in which the one end 8za of the liquid holding component 8z is wrapped around an external circumference of a bottom end portion of the conduction component 41z may be employed, or alternatively, a structure in which the one end 8za of the liquid holding component 8z is inserted through a through hole that is formed in the conduction component 41z may be employed. A material that is resistant to the measurement sample (i.e., that is chemical resistant), and that is capable of holding and being immersed in the measurement sample and the internal solution (for example, a hollow fiber) may be used for the liquid holding component 8z.

Moreover, in the second embodiment and the third embodiment as well, it is also possible for the measurement sample flow path, the reference electrode housing portion, and the connecting tubes and the like to be provided inside a block body.

Furthermore, when, for example, in addition to the hydrogen ion concentration, for example, the sodium ion or potassium ion concentration or the like are also being measured at the same time, then it is also possible to employ a structure in which a plurality of measurement electrodes that are suitable for the type of ions and the like that are to be measured are provided in parallel, and the measurement samples that have flowed from the measurement electrodes are merged together so that the reference electrode is common to each measurement electrode. Alternatively, it is also possible to provide a plurality of measurement electrodes in series so that the hydrogen ions, sodium ions, and potassium ions and the like can be measured in sequence, and to also provide a reference electrode so as to continue on from these in the same series so that the reference electrode is common to each measurement electrode. If this type of structure is used, then the measurement system can be made more compact and the concentration of a plurality of ions and the like can be measured simultaneously.

INDUSTRIAL APPLICABILITY

According to the present invention, it is possible to maintain conduction between an internal solution and a measurement sample in a liquid junction portion even if air bubbles are mixed into the measurement sample, and to enable the potential measurement of the measurement sample to be performed stably.

What is claimed is:

1. A reference electrode comprising:
   a body having an internal solution chamber that holds an internal solution, and a liquid junction portion that is disposed in the internal solution chamber such that the internal solution is in contact with a measurement sample that is to be measured; and
   an internal electrode that is disposed inside the internal solution chamber, wherein
   the liquid junction portion is formed by a conduction component that is formed by a porous or fibrous component, and an aperture that is provided separately from the conduction component at a position that is between the internal solution chamber and a flow path, and is adjacent to the conduction component, wherein
   the aperture is configured to receive the measurement sample,
   the conduction component is rod-shaped or cord-shaped and is provided in the internal solution chamber such that a longitudinal direction of the conduction component extends from the aperture toward the inside of the internal solution chamber,
   the internal solution chamber has an end portion that opens to the flow path,
   the conduction component is provided such that only part of the end portion is blocked, and
   the aperture is formed by a remainder of the end portion.

2. The reference electrode according to claim 1, wherein the conduction component is positioned such that the size of the aperture is larger than the size of holes formed in the conduction component.

3. The reference electrode according to claim 1, wherein an end portion of the conduction component that is in contact with the measurement sample is disposed such that this end portion is substantially flush with the aperture, or such that this end portion protrudes onto the measurement sample side beyond the aperture.

4. The reference electrode according to claim 1, wherein, when the measurement sample flows in one direction through a measurement sample holding portion that holds the measurement sample, the aperture is located on a downstream side of the flow of the measurement sample.

5. The reference electrode according to claim 4, wherein the measurement sample holding portion is positioned above the internal solution chamber, and above a top end of the internal electrode, and the internal solution chamber is formed such that a cross-sectional area of the internal solution chamber at a given distance from a top end portion of the internal solution chamber is smaller than a cross-sectional area of the internal solution chamber below the given distance.

6. The reference electrode according to claim 1, further comprising:
   a measurement sample holding portion that holds the measurement sample; and
   a connecting tube that connects together the internal solution chamber and the measurement sample holding portion, wherein
   the connecting tube is equipped with: a base tube portion; a first communicating tube portion that extends upwards from one end of the base tube portion and communicates with the measurement sample holding portion; and a second communicating tube portion that extends upwards from another end of the base tube portion and communicates with the internal solution chamber, or wherein
   the connecting tube is equipped with: a top tube portion; a first communicating tube portion that extends downwards from one end of the top tube portion and communicates with the measurement sample holding portion; and a second communicating tube portion that extends downwards from another end of the top tube portion and communicates with the internal solution chamber.

7. The reference electrode according to claim 6, wherein the connecting tube is connected to a lower side in a vertical direction of the measurement sample holding portion.

8. The reference electrode according to claim 6, further comprising a liquid holding component that is provided inside the connecting tube, wherein
   one end of the liquid holding component is provided in such a way as to be in contact with the conduction component, and another end of the liquid holding component is provided in the internal solution chamber.

9. The reference electrode according to claim 8, wherein the liquid holding component is a hollow fiber formed from a chemical resistant material.

* * * * *